US010744146B2

(12) United States Patent
Akimoto et al.

(10) Patent No.: US 10,744,146 B2
(45) Date of Patent: Aug. 18, 2020

(54) COMPOSITION HAVING EFFECTS OF PREVENTING OR AMELIORATING CONDITIONS OR DISEASES CAUSED BY BRAIN HYPOFUNCTION

(75) Inventors: Kengo Akimoto, Osaka (JP); Hiroshi Kawashima, Takatsuki (JP); Yoshiko Ono, Osaka (JP); Hiroshige Okaichi, Hirakata (JP); Youko Okaichi, Hirakata (JP)

(73) Assignee: SUNTORY HOLDINGS LIMITED, Osaka-shi, Osaka (JP)

( * ) Notice: Subject to any disclaimer, the term of this patent is extended or adjusted under 35 U.S.C. 154(b) by 826 days.

(21) Appl. No.: 10/485,456

(22) PCT Filed: Jan. 29, 2002

(86) PCT No.: PCT/JP02/00671
§ 371 (c)(1),
(2), (4) Date: Aug. 10, 2004

(87) PCT Pub. No.: WO03/013497
PCT Pub. Date: Feb. 20, 2003

(65) Prior Publication Data
US 2004/0266874 A1 Dec. 30, 2004

(30) Foreign Application Priority Data
Aug. 2, 2001 (JP) .................. 2001-235519

(51) Int. Cl.
*A23L 33/12* (2016.01)
*A23D 9/00* (2006.01)
*A23D 9/007* (2006.01)
*A23D 9/013* (2006.01)
*A23L 2/52* (2006.01)
*A61K 31/202* (2006.01)
*A61K 31/232* (2006.01)
*A61K 31/557* (2006.01)
*A61K 31/66* (2006.01)
*A61K 31/7024* (2006.01)

(52) U.S. Cl.
CPC ............ *A61K 31/7024* (2013.01); *A23D 9/00* (2013.01); *A23D 9/007* (2013.01); *A23D 9/013* (2013.01); *A23L 2/52* (2013.01); *A23L 33/12* (2016.08); *A61K 31/202* (2013.01); *A61K 31/232* (2013.01); *A61K 31/557* (2013.01); *A61K 31/66* (2013.01); *A23V 2002/00* (2013.01)

(58) Field of Classification Search
CPC .............. A61K 31/7024; A61K 31/202; A61K 31/232; A61K 31/557; A61K 31/66; A23L 33/12; A23L 2/52; A23D 9/00; A23D 9/007; A23D 9/013
USPC ....................................................... 514/547
See application file for complete search history.

(56) References Cited

U.S. PATENT DOCUMENTS

| 4,526,902 | A | 7/1985 | Rubin |
| 4,668,704 | A | 5/1987 | Hollander et al. |
| 5,198,468 | A | 3/1993 | Horrobin |
| 5,583,019 | A | 12/1996 | Barclay |
| 5,658,767 | A | 8/1997 | Kyle |
| 5,866,703 | A | 2/1999 | Horrobin et al. |
| 5,902,807 | A | 5/1999 | Haapalinna et al. |
| 6,034,130 | A | 3/2000 | Wang ............................ 514/558 |
| 6,069,138 | A | 5/2000 | Ponroy |
| 6,080,787 | A | 6/2000 | Carlson et al. |
| 6,225,444 | B1 | 5/2001 | Shashoua |
| 2002/0040058 | A1 | 4/2002 | Kiliaan et al. |
| 2003/0040542 | A1 | 2/2003 | Martin |
| 2004/0219208 | A1 | 11/2004 | Kawamura et al. |
| 2004/0266874 | A1 | 12/2004 | Akimoto et al. |
| 2006/0057185 | A1* | 3/2006 | Akimoto et al. ............. 424/439 |
| 2006/0088573 | A1 | 4/2006 | Ishikura et al. |
| 2006/0217368 | A1 | 9/2006 | Morishita et al. |

FOREIGN PATENT DOCUMENTS

| CA | 2109777 | 5/1994 | |
| CA | 2596241 | 12/1994 | |
| CA | 2 512 133 | 5/2005 | |
| CN | 1155982 A | 8/1997 | |
| CN | 1175976 | 3/1998 | |
| CN | 1205839 | 1/1999 | |
| EP | 0 296 751 | 12/1988 | |
| EP | 0 234 733 | 11/1991 | ............. A61K 33/00 |
| EP | 0 234 733 B1 | 11/1991 | |
| EP | 0 713 653 A1 | 5/1996 | |
| EP | 0 965 578 A1 | 12/1999 | |
| EP | 1 239 022 | 9/2002 | |

(Continued)

OTHER PUBLICATIONS

The Merk Manual, Fifteenth Edition, 1987, pp. 1421-1424.*

(Continued)

*Primary Examiner* — Yevgeny Valenrod
(74) *Attorney, Agent, or Firm* — Faegre Drinker Biddle & Reath LLP

(57) ABSTRACT

The object of the present invention is to provide a composition that has preventive or ameliorative action on symptoms or diseases caused by decreased brain function. This composition contains, as its active ingredient, arachidonic acid and/or a compound having arachidonic acid as a constituent fatty acid and, particularly, an alcohol ester of arachidonic acid or a triglyceride, phospholipid or glycolipid in which all or a portion of the constituent fatty acids are arachidonic acid.

20 Claims, 5 Drawing Sheets

(56) References Cited

FOREIGN PATENT DOCUMENTS

| | | | | |
|---|---|---|---|---|
| EP | 1 419 768 | | 5/2004 | |
| EP | 1 894 472 | A1 | 3/2008 | |
| GB | 0111282 | A | 1/2001 | |
| JP | S63297342 | A | 12/1988 | |
| JP | 64-22819 | | 1/1989 | |
| JP | 06256179 | | 9/1994 | |
| JP | 8-143454 | | 6/1996 | |
| JP | 08-214891 | A | 8/1996 | |
| JP | 8-511533 | | 12/1996 | |
| JP | 09-023817 | | 1/1997 | |
| JP | 09030962 | A | 2/1997 | |
| JP | 10-101568 | | 4/1998 | |
| JP | 10-155459 | | 6/1998 | |
| JP | 10-191886 | | 7/1998 | |
| JP | 11034236 | A | 2/1999 | |
| JP | 2000-8074 | | 1/2000 | |
| JP | 2000-516261 | | 12/2000 | |
| JP | 2001031586 | | 2/2001 | |
| JP | 2003048831 | | 2/2003 | |
| JP | 2003113120 | | 4/2003 | |
| JP | 2003504333 | | 2/2004 | |
| JP | 2005132758 | A | 5/2005 | |
| JP | 2006-502196 | | 1/2006 | |
| JP | 2006/076948 | | 3/2006 | |
| JP | 2006-83134 | | 3/2006 | |
| JP | 2006-83136 | | 3/2006 | |
| JP | 2006-521369 | | 9/2006 | |
| JP | 2007-8863 | | 1/2007 | |
| WO | 94/28913 | | 12/1994 | |
| WO | WO 94/28891 | | 12/1994 | |
| WO | WO 94/28913 | | 12/1994 | ............ A61K 37/00 |
| WO | WO 96/10922 | | 4/1996 | |
| WO | WO 96/21037 | A1 | 7/1996 | |
| WO | WO-9640106 | A2 | 12/1996 | |
| WO | WO-9726804 | A1 | 7/1997 | |
| WO | WO-9808501 | A1 | 3/1998 | |
| WO | WO 98/50052 | | 11/1998 | |
| WO | 00/21524 | | 4/2000 | |
| WO | WO 00/21524 | | 4/2000 | ............ A61K 31/20 |
| WO | WO 01/03696 | A1 | 1/2001 | |
| WO | WO-0124645 | A1 | 4/2001 | |
| WO | WO 01/85158 | A2 | 11/2001 | |
| WO | WO-0184961 | A2 | 11/2001 | |
| WO | WO 01/91745 | A2 | 12/2001 | |
| WO | WO 01/97793 | A2 | 12/2001 | |
| WO | WO 02/02105 | A1 | 1/2002 | |
| WO | WO 02/19839 | A1 | 3/2002 | |
| WO | 02/089787 | A1 | 11/2002 | |
| WO | WO 02/102394 | | 12/2002 | |
| WO | 03/004667 | | 1/2003 | |
| WO | WO 03/013497 | A1 | 2/2003 | |
| WO | WO-2003013497 | A1 | 2/2003 | |
| WO | 03/092673 | | 11/2003 | |
| WO | WO 2004/024136 | A1 | 3/2004 | |
| WO | WO 2004/024930 | A2 | 3/2004 | |
| WO | WO 2004/028529 | A1 | 4/2004 | |
| WO | WO 2004/084882 | A1 | 10/2004 | |
| WO | WO 2004/091663 | A1 | 10/2004 | |
| WO | 2005/018632 | | 3/2005 | |
| WO | WO 2005/037848 | A2 | 4/2005 | |
| WO | 2005/072306 | | 8/2005 | |
| WO | 2006/030552 | | 3/2006 | |

OTHER PUBLICATIONS

Nakawatase et al. "Alzheimer's Disease and Related Dementias." Cecil's Textbook of Medicine (Twenty-First Edition, vol. 1). W.B. Saunders Company, 2000. pp. 2042-2045.*
Yuksel et al. Etiologic classification of 4659 patients with mental retardation or multiple congenital abnormality and mental retardation. J. Pediatr. Neurosci. pp. 45-52, 2007.*
Simopoulos. Essential fatty acids in health and chronic disease. Am J Clin Nutr; 70 (Supply): 560-590S, 1999.*
Gorelick et al. Stroke prevention therapy beyond antithrombotics: unifying mechanisms in ischemic stroke pathogenesis and implications for therapy. Stroke. Mar. 2002.*
Happe et al. Time to give up on a single explanation for autism. Nat. Neurosci., Oct. 2006; 9(1): 1218-20.*
Belmonte et al. Fragile X syndrome and autism at the intersection of genetic and neural networks. Nat. Neurosci,. Oct. 2006, 9(10): 1221-5.*
Vericel et al. The influence of low intake of n-3 fatty acids on platelets in elderly people. Atherosclerosis, 147, pp. 187-192, 1999.*
ScienceDaily. Brain atrophy in elderly leads to unintended racism, depression and problem gambling. Association for Psychological Sciences, 2007.*
Vance [Editor]. Biochemistry of Lipids and Membranes, 1985, pp. 330-331.*
Danysz et al. The NMDA receptor antagonist memantine as a symptomatological and neuroprotective treatment for Alzheimer's disease: preclinical evidence. International Journal of Geriatric Psychiatry. 2003; 18: S23-S32.*
Fujita et al. Docosahexaenoic acid improves long-term potentiation attenuated by phospholipase A2 inhibitor in rat hippocampal slices. British Journal of Pharmacology, 2001, 132, 1417-1422.*
Youdim et al., "Essential fatty acids and the brain: possible health implications," *Int. J. Dev.* Neurosci, 2000, vol. 18, n.4, pp. 383-399, Elsevier, London, England (Abstract Only).
Youdim et al.; "Essential Fatty Acids and the Brain: Possible Health Implications"; *Int. J. Dev. Neurosci.*; Jul.-Aug. 2000; 18(4-5):383-399; PMID: 10817922 (Abstract only).
Kawashima et al., "Enzymatic Synthesis of High-Purity Structured Lipids with Caprylic Acid at 1,3-Positions and Polyunsaturated Fatty Acid at 2-Position," *JAOCS*, 2001, vol. 78, n. 6, AOCS Press, Champaign, IL.
Lynch, Marina, et al., "Impaired spatial memory in aged rats is associated with alterations in inositol phospholipid metabolism", NeuroReport, 1994, pp. 1493-1497, vol. 5, No. 12, American Society for Nutritional Sciences, Bethesda, Maryland.
Wainwright, P., et al., "Water Maze Performance Is Unaffected in Artificially reared Rats Fed Diets Supplemented with Arachidonic Acid and Docosahexaenoic Acid", J. Nutr., 1999, pp. 1079-1089, vol. 129, No. 5, American Society for Nutritional Sciences, Bethesda, Maryland.
Wainwright, P., et al. Arachidonic Acid Offsets the Effects on Mouse Brain and Behavior of a Diet with a Low (n-6)⊖ n-3) Ratio and Very High Levels of Docosahexaenoiuc Acid, J. Nutr., 1997, pp. 184-193, vol. 127, No. 1, American Society for Nutritional Sciences, Bethesda, Maryland.
Mackay & Mochly-Rosen, "Arachidonic Acid Protects Neonatal Rat Cardiac Myocytes from Ischaemic Injury though E Protein Kinase C," Cardiovascular Res. vol. 50, 2001, pp. 65-74, Elsevier Science B.V., Amsterdam, Holland.
Horrobin, "Abnormal Membrane Concentrations of 20 and 22-Carbon Essential Fatty Acids: A Common Link Between Risk Factors and Coronary and Peripheral Vascular Disease," Prostaglandins Leukot. Essent. Fatty Acids, vol. 53, 1995, pp. 385-396, Churchill Livingstone, Edinburgh, Scotland.
Webster's Third New International Dictionary, 1963, p. 1798, G.& C. Merriam Co., Springfield, MA.
Strub, "Vascular Dementia," South. Med. J., vol. 96, 2003, pp. 363-366, Southern Medical Association, Birmingham, AL.
Koletzko & Rodriguez-Palmero, "Polyunsaturated Fatty Acids in Human Milk and Their Role in Early Infant Development," J. Mammary Gland Biol. Neoplasia, vol. 4, 1999, pp. 269-284, Kluwer Academic/Plenum Publishers, New York, NY.
Carlson, "Docosahexaenoic Acid and Arachidonic Acid in Infant Development," Semin. Neonatol., vol. 6, 2001, pp. 437-449, Elsevier Science Ltd., Amsterdam, Holland.
Auestad et al., "Visual, Cognitive, and Language Assessments at 39 Months: A Follow up Study of Children Fed Formulas Containing Long-Chain Polyunsaturated Fatty Acids to 1 Year of Age," Pediatrics, vol. 112, 2003, pp. e177-e183, American Academy of Pediatrics, Elk Grove Village, IL.

(56) References Cited

OTHER PUBLICATIONS

Willatts et al., "Effect of Long-Chain Polyunsaturated Fatty Acids in Infant Formula on Problem Solving at 10 Months of Age," Lancet, vol. 352, 1998, pp. 688-691, Lancet, Publishing Group, London, England.
Lucas et al., "Efficacy and Safety of Long-Chain Polyunsaturated Fatty Acid Supplementation of Infant-Formula Milk: A Randomized Trial," Lancet, vol. 354, 1999, pp. 1948-1954, Lancet, Publishing Group, London, England.
McGahon et al., "The Ability of Aged Rats to Sustain Long-Term Potentiation is Restored When the Age-Related Decrease in Membrane Arachidonic Acid Concentration is Reversed," Neuroscience, vol. 81, 1997, pp. 9-16, Elsevier Science Ltd., Amsterdam, Holland.
K. Naliwaiko et al., "Effects of Fish Oil on the Central Nervous System: A New Potential Antidepressant?" Nutritional Neuroscience, vol. 7, No. 2, pp. 91-99 (2004).
Office Action dated Feb. 17, 2011 issued in corresponding Chinese Patent Application. No. 200480001751.X (with English translation).
Russian Office Action dated Sep. 14, 2011 in Russian Application No. 2008103361/15(003664) with English language translation.
Bolshaya Rossijskaya Entsyclopediya, 1992, vol. 3, p. 202 (w/ English translation).
Korean Office Action dated Sep. 27, 2011 in Korean Application No. 7005102/2005 with English language translation.
Gordon, "Nutrition and Cognitive Function", Brian and Development, vol. 19, (1997), pp. 165-170.
Susumu Kotani et al., "Improvement of Synaptic Plasticity in the Hippocampus of Aged Rats by Ingestion of Arachidonic Acid," 24th Japan Neurosurgical Socity Program, 2001, p. 243. (in Japanese w/English translation).
Hart et al., "The Contribution Risk Factors to Stroke Differentials, by Socioeconomic Position in Adulthood: The Renfrew/Paisley Study," Am. J. of Public Health, vol. 90, No. 11 (Nov. 2000), pp. 1788-1791.
Kelly et al., "Arachidonic Acid Supplementation Enchances Synthesis of Eicosanoids without Suppressing Immune Functions in Young Healthy Men," Lipids, vol. 33, No. 2 (1998) pp. 124-130.
McGahon et al., "Age-Related Changes in Synaptic Function: Analysis of the Effect of Dietary Supplementation with ω-3 Fatty Acids," Neuroscience, vol. 94, No. 1, 1999, pp. 305-314.
Office Action dated Jun. 28, 2010 in European Patent Application No. 03 748 553.9.
Office Action dated Mar. 27, 2008 in U.S. Appl. No. 10/529,014.
Office Action dated Jul. 3, 2008 in U.S. Appl. No. 10/529,014.
Office Action dated Mar. 2, 2009 in U.S. Appl. No. 10/529,014.
Office Action dated Apr. 13, 2010 in U.S. Appl. No. 10/529,014.
Office Action dated Oct. 2, 2007 in U.S. Appl. No. 10/541,073.
Office Action dated Jan. 16, 2008 in U.S. Appl. No. 10/541,073.
Office Action dated Nov. 26, 2008 in U.S. Appl. No. 10/541,073.
Advisory Action dated Jun. 3, 2009 in U.S. Appl. No. 10/541,073.
McNamara et al., "The Neuropharmacological and Neurochemical Basis of Place Learning in the Morris Water Water Maze," Brain Res. Rev., vol. 18, pp. 33-49 (1993).
Reddy, "Preclinical and Clincal Behavioral Paradigms for Testing Drugs that Affect Learning and Memory Processes," Methods Find. Exp. Clin. Pharmacol. vol. 20, No. 3, pp. 249-277 (1998).
Written Opinion dated Nov. 7, 2006 in International PCT Application PCT/JP2006/313444 filed Jun. 29, 2006.
Office Action dated Jan. 26, 2010 in Russian Application No. 2008103361/15(003664) with English language translation.
Search Report dated Nov. 7, 2006 for International Application No. PCT/JP2006/313444 filed Jun. 29, 2006.
Louis-Joseph Auguste et al., "Prevention of Stress-Induced Erosive Gastritis by Parenteral Administration of Arachidonic Acid", Journal of Parenteral and Enteral Nutrition, vol. 14, No. 6, 1990, pp. 615-617.
Search Report dated Jul. 20, 2005 for International Patent Application No. PCT/JP2005/005622 filed Mar. 18, 2005.

John R. Burgess et al.; "Long-Chain Polyunsaturated Fatty Acids in Children With Attention-Deficit Hyperactivity Disorder"; American Journal of Clinical Nutrition, Bethesda, MD, US, vol. 71, No. 1, Suppl, Jan. 2000, pp. 237S-330S; XP008000462.
Search Report dated Jul. 11, 2005 from International PCT Application No. PCT/JP2005/005623.
Susumu Kotani et al., "Dietary supplementation of arachidonic and docosahexaenoic acids improves cognitive dysfunction," 2006, pp. 159-164, vol. 56, Neuroscience Research, Limerick, Ireland.
Search Report dated Mar. 4, 2008 for International Application No. PCT/JP2007/075403 filed Dec. 27, 2007.
Yoshimura et al., "FGF-2 regulation of neurogenesis in adult hippocampus after brain injury," PNAS, May 8, 2001, vol. 98, No. 10, pp. 5874-5879.
Nakatomi et al., "Regeneration of Hippocampal Pyramidal Neurons after Ischemic Brain Injury by Recruitment of Endogenous Neural Progenitors," Cell, vol. 110, Aug. 23, 2002, pp. 429-441.
Kawakita et al., "Docosahexaenoic Acid Promotes Neurogenesis in Vitro and in Vivo," Neuroscience, 2006, vol. 139, pp. 991-997.
Hirano et al., "Influence of Taurine Load on Neural Development," Program of the 173rd Meeting of the Essential Amino Acid Research Council, 2003, p. 1 (with partial English-language translation).
European Search Report dated Jan. 27, 2010 in EP Application No. 07860598.7.
Search Report dated Jan. 31, 2007 for International Application No. PCT/JP2006/313437 filed Jun. 29, 2006.
Database WPI Week 200064, Derwent Publications Ltd., London, GB; AN 2000-658544, XP002410776.
Choi-Kwon, Smi et al., "Temporal changes in cerebral antioxidant enzyme activities after ischemia and reperfusion in a rat focal brain ischemia model: effect of dietary fish oil," Developmental Brain Research, Aug. 18, 2004, pp. 11-18, vol. 152, No. 1, XP007901417.
Office Action dated Sep. 3, 2010 in Russian Patent Application No. 2008103361/15(003664) (with English translation).
Psychiatry edited by R. Sheider, Moscow, Praktika, 1998, pp. 280-282 and 287-289 (with English Translation).
Japanese Office Action dated Jan. 12, 2010 issued in Japanese application No. 2004-539481.
Office Action dated Sep. 22, 2011 issued in Australian Patent Application No. 2005283697.
Stevens et al., "EFA Supplementation in Children with Inattention, Hyperactivity, and Other Disruptive Behaviors," Lipids, vol. 38, No. 10, (2003), pp. 1007-1021.
Song et al., "Effects of dietary n-3 or n-6 fatty acids on interleukin-lb-induced anxiety, stress, and inflammatory responses in rats," *Journal of Lipid Research*, Oct. 2003, vol. 44, No. 10, pp. 1984-1991 (electronically published Jul. 1, 2003).
Mills et al., "Psychosocial stress, catecholamines, and essential fatty acid metabolism in rats," Proc. Soc. Exp. Biol. Med., Jan. 1994, vol. 205, No. 1, pp. 56-61.
Wollan et al., "Dietary essential fatty acids and gender-specific difference in rat maze learning and memory," Neuroscience Abstract, 2000, No. 793.13, Society for Neuroscience, vol. 26.
Kawashima et al., "Enzymatic Synthesis of High-Purity Structured Lipids with Caprylic Acid at 1,3-Positions and Polyunsaturated Fatty Acid at 2-Position," JAOCS, vol. 78, No. 6 (2001).
European Office Action dated May 2, 2011 in European Patent Application No. 06780813.9.
Ulmann et al., "Brain and hippocampus fatty acid composition in phospholipid classes of aged-relative cognitive deficit rats," Prostaglandins, Leukotrienes and Essential Fatty Acids, vol. 64, Issue 3, Mar. 2001 (abstract).
The Merck Manual of Diagnosis and Therapy, 18th Ed., Merck Research Laboratories, 2006, pp. 1816-1818.
Aronen et al., "Motor activity and severity of depression in hospitalized prepubertal children," J Am. Acad. Child Adolesc. Psychiatry, Jun. 1996; 35(6): 752-763.
Yakkyoku (Pharmacy), 2000, vol. 51, No. 2, p. 2-10 (w/partial English Translation).
Modern Physician, 2002, vol. 22, No. 9, p. 1155-1157 (w/partial English translation).

(56) References Cited

OTHER PUBLICATIONS

Randolph, "Repeatable Battery for the Assessment of Neuropsychological Status (RBANS™)," available at http://www.pearsonassessments.com/HAIWEB/Cultures/en-us/Productdetail.htm?Pid=015-8166-000 (last visited Jul. 3, 2012).

Golfetto et al., Nutr. Neurosci., 2001, 4(1), 75-79, abstract.

Supplementary European Search Report dated Aug. 30, 2010, issued in European patent application No. GPS/FP6312367.

Kark et al., "Adipose Tissue n-6 Fatty Acids and Acute Myocardial Infarction in a Population Consuming a Diet High in Polyunsaturated Fatty Acids", *Am J Clin Nutr*, 77, 796-802 (2003).

Minami et al., "Dietary Decosahexaenoic Acid Increases Cerebral Acetylcholine Levels and Improves Passive Avoidance Performance in Stroke-Prone Spontaneously Hypertensive Rats," Pharmacology Biochemistry and Behavior, vol. 58, No. 4, pp. 1123-1129 (1997).

The Merck Manual of Diagnosis and Therapy, 18th Ed., Merck Research Laboratories, 2006, pp. 1816-1819.

Novel Food Information—DHASCO® and ARASCO® from Health Canada, Date Modified Jan. 31, 2003.

Lynch, "Analysis of the Mechanisms Underlying the Age-related Impairment in Long-Term Potentiation in the Rat," Reviews in the Neurosciences, vol. 9, pp. 169-201 (1998).

Anderson et al., "Breast-feeding and cognitive development: a meta-analysis," Am. J. Clin. Nutr., vol. 70, pp. 525-535 (1999).

Crawford, "The role of essential fatty acids in neural development: implications for perinatal nutrition," Am. J. Clin. Nutr., pp. 703S-710S, vol. 57 (suppl) (1993).

Crawford et al., "Are deficits of arachidonic and docosahexaenoic acids responsible for the neural and vascular complications of preterm babies?," Am. J. Clin. Nutr., vol. 66 (suppl), pp. 1032S-1041S (1997).

Hempenius et al., "Preliminary Safety Assessment of an Arachidonic Acid-enriched Oil derived from *Mortierella alpine*: Summary of Toxicological Data," Food and Chemical Toxicology, vol. 35, pp. 573-581 (1997).

Birch et al., "A randomized controlled trial of early dietary supply of long-chain polyunsaturated fatty acids and mental development in term infants," Developmental Medicine & Child Neurology, vol. 42, pp. 174-181 (2000).

Kalmijn et al., "Dietary Fat Intake and the Risk of Incident Dementia in the Rotterdam Study," Annals of Neurology, pp. 776-782 (1997).

Soderberg et al., "Fatty Acid Composition of Brain Phospholipids in Aging and in Alzheimer's Disease," Lipids, vol. 26, No. 6, pp. 421-425 (1991).

Fields, Letter to Food and Drug Administration, Aug. 27, 1998, "Re: Notice of a Claim for Exemption From Premarket Approval," available at http://www.accessdata.fda.gov/scripts/fcn/gras_notices/grn_7.pdf, documents created in 1998.

Ferguson, Letter to Linda Kahl, Ph.D., Aug. 3, 2001, "Re: GRAS Notice for ARASCO® (arachidonic acid-rich single-cell oil) Level in Term Infant Formula."

Wieraszko, "Avian Hippocampus as a Model to Study Spatial Orientation-Related Synaptic Plasticity," Molecular and Cellular Mechanisms of Neuronal Plasticity, pp. 107-129 (1998).

Notice of Opposition against EP1419768 by Abbott Laboratories (May 17, 2012).

Notice of Opposition against EP 1419768 by N.V. Nutricia (May 16, 2012).

GlaxoWellcom, "Zung Self-Rating Depression Scale," 1997.

Notice of Opposition against EP 1542670 filed by N.V. Nutricia (Feb. 27, 2014).

McGahon, et al., "Age-related changes in oxidative mechanisms and LTP are reversed by dietary manipulation", Neurobiology of Aging 20 (1999) pp. 643-653.

McGahon, et al., "Training in the Morris Water Maze Occludes the Synergism Between ACPD and Arachidonic Acid on Glutamate Release in Synaptosomes Prepared from Rat Hippocampus", Learning Memory 1996 3: 296-304.

Kotani, et al., "Diet of Arachidonic Acid Improved Synaptic Plasticity in Aged Rat Hippocampal CA1 Neuron", Neuroscience, 316.13, Nov. 12, 2001 (Abstract).

Beukers, et al., "Pharmacology of long-term potentiation—A model for learing reviewed", Pharm Weekbl[Sci] 1991; 13(1), pp. 7-12.

Horimoto, et al., "Arachidonic Acid Activation of Potassium Channels in Rat Visual Cortex Neurons", Neuroscience, 1997, vol. 77, No. 3, pp. 661-671.

Bach, et al., "Medium-chain triglycerides: an update", The American Journal of Clinical Nutrition 36: Nov. 1982, pp. 950-962.

Japanese Office Action dated May 20, 2014 in JP 2005-191624 (in Japanese).

Yamashima et al., "Evaluation of higher-order brain function by RBANS neuropsychological test," Brain and Nerve, 54(6): 463-471 (2002) (with partial English translation).

Decision Revoking the European Patent dated Nov. 25, 2014, in EP Patent No. 1 419 768.

Umeda-Sawada et al., "Distribution and Metabolism of Dihomo-γ-linolenic Acid (DGLA 20:30n-6) by Oral Supplementation in Rats", Biosci. Blotechnol. Biochem., 2006, 70 (9), 2121-2130.

Wang, et al., "The flavonoid baicalein promotes NMDA receptor-dependent long-term potentiation and enhances memory", British Journal of Pharmacology, 2011, 162, 1364-1379.

Park, et al., "Mismatch between changes in baicalein-induced memory-related biochemical parameters and behavioral consequences in mouse", Brain Research, 2010, 1355, 141-150.

Casey, et al., "Analysis of the Presynaptic Signaling Mechanisms Underlying the Inhibition of LTP in Rat Dentate Gyrus by the Tyrosine Kinase Inhibitor, Genistein", Hippocampus, 2002, 12:377-385.

Huang, et al., "Genistein reduced the neural apoptosis in the brain of ovariectomised rats by modulating mitochondrial oxidative stress", British Journal of Nutrition, 2010, 104, 1297-1303.

Lathe, "Hormones and the hippocampus", Journal of Endocrinology, 2001, 169, 205-231.

Llenalia Garcia Fernández, "Statistical Issues for Patent Specification EP 1 419 768 B1", Jun. 2013.

Gitto, et al., "The patient with Alzheimer's disease", Quintessence International, Nov. 3, 2001, 32:221-231.

P. Srinivas, "Diagnosis and Management of Alzheimer's Disease—An Update", Med J Malaysia, Dec. 1999, vol. 54, No. 4, pp. 541-550.

CNS Neurotransmitters & Neuromodulators: Acetycholine, 1994, ed. Trevor W. Stone, pp. 39-47 (Monferini, "Subtypes of Neuronal Muscarinic Receptors: Pharmacological Criteria"); p. 204.

Bliss, et al., "A synaptic model of memory: long-term potentiation in the hippocampus", Nature, Jan. 7, 1993, 361:31-39.

Martinez, et al., "Long-Term Potentiation and Learning", Annu. Rev. Psychol, 1996, 47:173-203.

Will Block, "Protect Brain Function by Enhancing Vascular Health," Aug. 2001, available at http://www.life-enhancement.com/magazine/article/594-protect-brain-function-by-enhancing-vascular-health.

Japanese Office Action dated Jun. 4, 2013 issued in corresponding Japanese Patent Application No. 2011-230136 (in Japanese).

KR Application 10-2004-7001544—Notification of Reason for Refusal dated Aug. 16, 2016.

J. Strosznajder, et al., "Aging Diminishes Serotonin-Stimulated Arachidonic Acid Uptake and Cholinergic Receptor-Activated Arachidonic Acid Release in Rat Brain Cortex Membrane", Journal of Neurochemistry, 1994, vol. 62, pp. 1048-1054.

Office Action dated Mar. 2, 2010 in Japanese Patent Application JP2004-539481.

Werring et al. Brain, 2004, vol. 127, Pt 10, pp. 1-11.

McCrory et al. Br. J. Sports. Med., vol. 39, Published Mar. 2005, pp. 196-204.

CN Application 20140745897.0—Office Action dated Jun. 3, 2016.

Hilbush, B.S., et al., NeuroRx: The Journal of the American Society for Experimental NeuroTherapeutics, 2, 627-637, 2005.

Kawashima, H., et al., "Oral Administration of Dihomo-γ-Linolenic Acid Prevents Development of Atopic Dermatitis in NC/Nga Mice," *Lipids* 43: 37-43 (2008).

Jokinen et al., "Cognitive profile of subcortical ischaemic vascular disease", J. Neurol Neurosurg. Psychiatry, 2006, vol. 77, pp. 28-33.

(56) References Cited

OTHER PUBLICATIONS

Bremner, "Traumatic stress: effects on the brain", J. Dialogues Clin. Neurosci., 2006, vol. 8, pp. 445-461.
Kapoor et al., Gamma Linolenic Acid Oils, in Part 3. Edible Oil & Fat Products: Specialty Oils and Oil Products, John Wiley & Son, Inc., 2005, pp. 67-119.
Patterson, J. Nutr. Metab. 2012: 539426 (2012).
Bézard et al., 34 Reprod. Nutr. Dev. 539 (1994).
Nakamura et al., 145 Prostaglandins Leukot. Essent. Fatty Acids 145 (2003).
Willis et al., in New Protective Roles for Selected Nutrients, Ed. Alan R. Liss, New York, 1989, pp. 39-108.
Robinson et al., 20 Prostaglandins Leukot. Med. 209 (1985).
Rett et al., 8 Nutr. Metab. (Lond.) 36 (2011).
DeVries et al., 22 J. Lipid Res. 208 (1981).
Makrides et al., 60 Am. J. Clin. Nutr. 189 (1994).
Farquharson et al., 72 Arch. Dis. Child. 198 (1995).

\* cited by examiner

COMPOSITION HAVING EFFECTS OF PREVENTING OR AMELIORATING CONDITIONS OR DISEASES CAUSED BY BRAIN HYPOFUNCTION

This application is a national stage filing under 35 U.S.C. § 371 of International Application No. PCT/JP02/00671, filed on Jan. 29, 2002, the entire contents of which are incorporated herein in its entirety.

BACKGROUND OF THE INVENTION

Technical Field

The present invention relates to a composition, and its production method, that has preventive or ameliorative action on symptoms or diseases caused by decreased brain function, having for its active ingredient arachidonic acid and/or a compound having arachidonic acid as its constituent fatty acid. More particularly, the present invention relates to a preventive or ameliorant for decreased memory or learning ability, decreased cognitive ability, emotional disorders (e.g., depression) and mental disorders (e.g., dementia, and specifically Alzheimer's dementia, and cerebrovascular dementia), a composition that has preventive or ameliorative action and a production method thereof, having for its active ingredient at least one type selected from the group consisting of arachidonic acid, alcohol esters of arachidonic acid, and triglycerides, phospholipids and glycolipids in which a portion or all of the constituent fatty acid is arachidonic acid.

Background Art

There has been a sudden increase in the proportion of elderly persons in society, in recent years, accompanying advances made in the field of medicine. This is resulting in a corresponding increase in the number of persons suffering from senile dementia. According to the "Annual Report on Health and Welfare 1999-2000" and the "Report on the Study of Countermeasures for Elderly Persons with Dementia", the number of elderly suffering from dementia during the 2000 fiscal year was 1.5-1.6 million, and the number of dementia patients age 65 and over reached 1 in 14 persons. The number of these patients is predicted to increase to 1 in 10 persons by 2030. As senile dementia progresses, it causes impairment of mental functions and emotions, eventually causing problems in terms of everyday life and social activities. The causes of senile dementia can be divided into cerebrovascular dementia, Alzheimer's dementia and combinations thereof. Although research and development activities have been conducted on drugs effective for the treatment of these brain disorders (including those that improve cerebral circulation and metabolism as well as those that inhibit dementia), an effective therapeutic drug has yet to be found. Although cerebral infarctions occur to a certain extent as people age, the occurrence of dementia can be prevented by, for example, using the brain. In consideration of this, it is thought to be quite possible to develop drugs targeted at not only treatment, but prevention as well. However, a drug that is safe and can be taken easily by persons ranging from infants to the elderly, inhibits decreases in brain function, prevents symptoms or disease's caused by decreases in brain function and exhibits ameliorative effects has, essentially, not yet been developed.

Research studies have been conducted in the past on methods for improving brain function, examples of which include a method for improving the metabolism of brain energy that activates the functions of cells by allowing brain cells to efficiently absorb nutrients (such as by elevating brain glucose levels), a method for improving cerebral circulation for the purpose of adequately supplying necessary nutrients and oxygen to brain cells by improving cerebral blood flow (such as by increasing cerebral blood flow volume), and a method for activating neurotransmission that takes place in synaptic gaps mediated by neurotransmitters (by supplying precursors of neurotransmitters (e.g., by supplementing with choline or acetyl CoA), inhibiting conversion of released neurotransmitters (e.g., by inhibiting acetylcholinesterase), increasing release of neurotransmitters (e.g., by increasing the release of acetylcholine or glutamic acid) or activating neurotransmitter receptors), and protecting nerve cell membranes (by, for example, antioxidation, supplying membrane components and preventing arteriosclerosis).

During the course of this past research, although ingredients that prevent symptoms or diseases caused by decreased brain function as well as ingredients that have ameliorative effects have been found, their effectiveness remains doubtful at the present time, and an effective drug has yet to be found for use as a pharmaceutical. Moreover, in the case of considering applications to foods, there has also been the additional difficulty of being limited to ingredients of natural origin.

The brain consists of tissue that resembles a mass of lipids. For example, phospholipids account for one-third of the tissue that comprises white matter and one-fourth of the tissue that comprises gray matter. The polyunsaturated fatty acids in the phospholipids that compose the various cell membranes of brain cells consist primarily of arachidonic acid and docosahexaenoic acid. However, this arachidonic acid and docosahexaenoic acid cannot be synthesized de novo by animals, and must be ingested from the diet either directly or indirectly (as linoleic acid and α-linolenic acid that are precursors of arachidonic acid and docosahexaenoic acid). Therefore, attention is being focused on the improvement of learning and memory abilities and the prevention and recovery of senile dementia associated with docosahexaenoic acid. However, among the major fatty acids of phospholipids of the brain, not only docosahexaenoic acid, but also arachidonic acid is an important fatty acid that is present in roughly the same degree. Sonderdegr, et al. determined that, in contrast to the proportion of arachidonic acid in phospholipids of the hippocampus being 12.4% by weight in normal individuals, that proportion decreases significantly to 8.1% by weight in Alzheimer's patients (Lipids, 26, 421-425, 1991). In this manner, although this suggests that arachidonic acid has the potential for playing an important role in maintaining brain function, concrete evidence has yet to be presented.

Several inventions have been indicated that utilize arachidonic acid for maintaining brain function. The "learning ability improver" described in Japanese Unexamined Patent Publication No. 6-256179 is an invention that has for its active ingredient a 1,2-diacyl-sn-glycerol derivative, various polyunsaturated fatty acids bound at 2-position are listed, and arachidonic acid is indicated as one of those fatty acids. However, only a 1,2-diacyl-sn-glycerol derivative in which docosahexaenoic acid is bound is specifically indicated in the examples, while arachidonic is listed only without any demonstration of its effect. A novel brain function ameliorant and a combination of ganglioside and arachidonic acid as a means for supplying a nutrient composition that contains the same are indicated in a "brain function ameliorant and nutrient composition" described in Japanese Unexamined Patent Publication No. 10-101568. However, although an experiment using naturally aged rats is indicated as a test example, the age of the rats at testing is only 13 months, which is equivalent to a human age of 33 years (one day for rats is equivalent to one month for humans), thus making it difficult to consider such a test as indicative of an aging model. In addition, the proportion or amount of arachidonic acid in brain phospholipid typically does not exhibit any changes at this age, and since decreases in brain function caused by aging are also not observed at this age, the effects of arachidonic acid would typically be considered to be unlikely to occur. In actuality, the effect of arachidonic acid alone was not evaluated in the test example, and it was merely indicated that arachidonic acid enhances the effect of ganglioside.

The "protein kinase C isozyme activator" described in Japanese Unexamined Patent Publication No. 6-279311 indicates the activation of protein kinase C, which plays an important role in intracellular information transmission, and a senile dementia therapeutic drug as its accompanying effect. However, the active ingredient is a phosphatidyl serine derivative having polyunsaturated fatty acids as its constituent fatty acids, and one of those polyunsaturated fatty acids is arachidonic acid. In the examples, however, there are no large differences in the effect of arachidonic acid between phosphatidyl serine derivatives bound with linoleic acid and α-linolenic acid, there is no superiority of phosphatidyl serine derivatives having arachidonic acid as a constituent fatty acid, and the effect of arachidonic acid is not demonstrated. In addition, as evaluation consists only of measurement of enzyme activity, preventive or ameliorative effects on symptoms or diseases caused by decreased brain function are not clarified. In this manner, although several inventions have been indicated that utilize arachidonic acid to maintain brain function, since arachidonic acid and compounds having arachidonic acid as a constituent fatty acid were not supplied in adequate amounts, the inventors are unable to identify the true effects in animal experiments and so forth, and merely describe arachidonic acid as one member of a group of fatty acids, thereby preventing them from providing a description of the actual state.

Short-term and long-term memory loss, which are pathological memory disorders accompanying organic lesions in the brain, are a core symptom of dementia. However, forgetfulness, which is another word for memory disorder, is one of the most frequently observed complaints among the elderly, and decreases in learning and memory abilities in humans accompanying physiological aging has been indicated in various research (Katzman, R. and Terry, R., The Neurology of Aging, F. A. Davis, Philadelphia, pp. 15-50).

In looking at memory in terms of the passage of time during which memories are formed, memory can be classified into sensory memory, primary memory and secondary memory. Primary memory may also be referred to as immediate memory, while secondary memory may be referred to as long-term memory. Short-term memory may refer to primary memory as well as learning ability that also covers secondary memory. Although sensory memory is formed when there is visual input that persists for about 50 milliseconds, it is extremely unstable and ends up being lost within 250-500 milliseconds. Primary memory is retained while the subject is constantly aware of it during the time information is recognized and processed, and fulfills the role of working memory. After information that has been processed as primary memory is transferred to secondary memory and retained for a long period of time, it is again recalled by way of primary memory. Since primary memory has a very small capacity, it ends up being lost in 20-30 seconds unless it is repeatedly recalled. Secondary memory is composed of each of the steps of transfer of information processed with primary memory, consolidation, its semi-permanent storage and its retrieval. This secondary memory is considerably impaired with aging. Since this decrease in secondary memory is mainly the result of impairment at the stage up to and including memory storage, there is hardly any decline observed with respect to the ability to retrieve memories stored in youth. However, in patients with dementia, this memory is also constantly subject to impairment.

One of the effects of arachidonic acid has been clearly determined from electrophysiological analysis. A phenomenon is known to occur in which, when stimuli are applied to the hippocampus at a high frequency to excite the synapses, the subsequent synaptic responses are maintained at a high level. This phenomenon is referred to as hippocampus LTP (long-term potentiation). It is based on the reversible nature of synapses and is used as an indicator for assessment of brain function. B. M. McGahon, et al. measured the hippocampus LTP in rats housed for 8 weeks while feeding the animals a control diet or a diet containing arachidonic acid (10 mg/rat/day) using 22-month-old old rats (Neurobiol. Aging, 20, 643, 1999). In comparison with 4-month-old young rats, the hippocampus LTP levels of the old rats decreased sharply, and demonstrated a recovery to the level of young rats due to administration of arachidonic acid. However, in terms of the memory mechanism, this enhancement of hippocampus LTP indicates activation of primary memory, and not activation of a shift from primary memory to secondary memory required for memory fixation. Thus, effects on memory fixation cannot be verified unless they are clarified in a behavioral pharmacology study. In this manner, although examples of assessing the effects of arachidonic acid using electrophysiological indicators have been indicated, whether or not arachidonic acid and/or compounds having arachidonic acid as a constituent fatty acid of the present invention are effective for the prevention or amelioration of symptoms or diseases caused by decreased brain function has not been determined.

Thus, there is a strong need to develop pharmaceuticals and safer compounds, superior for application to foods, that prevent and exhibit ameliorative effects on symptoms or diseases caused by decreased brain function.

DISCLOSURE OF THE INVENTION

Thus, an object of the present invention is to provide a preventive or ameliorant for symptoms or diseases caused by decreased brain function, a food or beverage that has preventive or ameliorative action on symptoms or diseases caused by decreased brain function, and a production method thereof, which have for their active ingredient arachidonic acid and/or a compound having arachidonic acid as a constituent fatty acid. More particularly, an object of the present invention is to provide a preventive or ameliorant for decreased memory or learning ability, decreased cognitive ability, emotional disorders (e.g., depression) and mental disorders (e.g., dementia, and specifically Alzheimer's dementia, and cerebrovascular dementia), a food or beverage having said preventive or ameliorative action, and a production method thereof, which have for their active ingredient at least one type selected from the group consisting of arachidonic acid, alcohol esters of arachidonic acid, and triglycerides, phospholipids and glycolipids in which all or a portion of the constituent fatty acids are arachidonic acid.

As a result of conducting extensive research for the purpose of determining the preventive or ameliorative effects of arachidonic acid or compounds having arachidonic acid as a constituent fatty acid on symptoms or diseases caused by decreased brain function, the inventors of the present invention unexpectedly determined the effects of arachidonic acid or compounds having arachidonic acid as a constituent fatty acid through a behavioral pathology analysis by using old rats more than 20 months old in a Morris water maze test.

Moreover, the inventors of the present invention succeeded in industrially producing triglyceride having an arachidonic content of 20% by weight or more using microorganisms, were able to use this for testing the effects of the present invention, and determined the effects of said triglyceride.

Moreover, the inventors of the present invention also succeeded in producing oils and fats containing triglyceride in which medium-chain fatty acids are bound at 1,3-position and arachidonic acid is bound at 2-position, were able to use this for testing the effects of the present invention, and determined the effects of said triglyceride.

Thus, the present invention provides a preventive or ameliorant for symptoms or diseases caused by decreased brain function, a food or beverage having preventive or ameliorative action on symptoms or diseases caused by decreased brain function, and a production method thereof, which have for their active ingredient arachidonic acid and/or a compound having arachidonic acid as a constituent fatty acid. More particularly, the present invention provides a preventive or ameliorant for decreased memory or learning ability, decreased cognitive ability, emotional disorders (e.g., depression) and mental disorders (e.g., dementia, and specifically Alzheimer's dementia, and cerebrovascular dementia), a food or beverage having said preventive or ameliorative action, and a production method thereof, which have for their active ingredient at least one type selected from the group consisting of arachidonic acid, alcohol esters of arachidonic acid, and triglycerides, phospholipids and glycolipids in which all or a portion of the constituent fatty acids are arachidonic acid.

As a result of the present invention, a preventive or ameliorant for symptoms or diseases caused by decreased brain function, a food or beverage having preventive or ameliorative action on symptoms or diseases caused by decreased brain function, and a production method thereof, which have for their active ingredient arachidonic acid and/or a compound having arachidonic acid as a constituent fatty acid, can be provided, and are particularly useful for all humans considering the growing size of the elderly population throughout society.

BEST MODE FOR CARRYING OUT THE INVENTION

Figure 1:
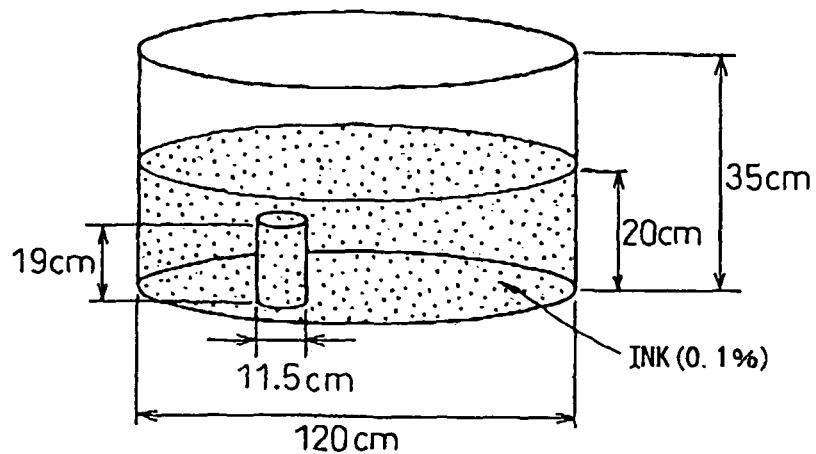
FIG. 1 is a schematic explanatory drawing of a device used for a Morris water maze test.

The present invention relates to a preventive or ameliorant for symptoms or diseases caused by decreased brain function, a food or beverage having preventive or ameliorative action on symptoms or diseases caused by decreased brain function, and a production method thereof, which have for their active ingredient arachidonic acid and/or a compound having arachidonic acid as a constituent fatty acid.

The composition of the present invention has preventive or ameliorative action on symptoms or diseases caused by decreased brain function, and is useful as a food or beverage, pharmaceutical or over-the-counter drug and so forth for the purpose of prevention and amelioration (or treatment) of decreased memory or learning ability, decreased cognitive ability, emotional disorders (e.g., depression) and mental disorders (e.g., dementia, and specifically Alzheimer's dementia, and cerebrovascular dementia).

More specifically, the compound of the present invention has preventive or ameliorative action on symptoms or diseases caused by decreased brain function accompanying aging, is useful as a food or beverage, pharmaceutical or over-the-counter drug and so forth for the purpose of prevention and amelioration (or treatment) of decreased memory or learning ability, decreased cognitive ability, emotional disorders (e.g., depression) and mental disorders (e.g., dementia, and specifically Alzheimer's dementia, and cerebrovascular dementia), and is useful as a food or beverage, health food, functional food, food for specified health uses or geriatric food for the purpose preventing forgetfulness, preventing senility, maintaining and improving memory, maintaining and improving concentration, maintaining and improving attentiveness, refreshing the mind, maintaining wakefulness and maintaining youth.

In addition to free arachidonic acid, all compounds having arachidonic acid as a constituent fatty acid can be used for the active ingredient of the present invention. Examples of compounds having arachidonic acid as a constituent fatty acid include salts of arachidonic acid such as calcium salts and sodium salts. Other examples include alcohol esters of arachidonic acid such as arachidonate methyl ester and arachidonate ethyl ester. In addition, triglycerides, phospholipids and glycolipids in which all or a portion of their constituent fatty acids are arachidonic acid can also be used.

In the case of considering applications to foods, arachidonic acid is preferably in the form of a triglyceride or phospholipid, and particularly preferably in the form of a triglyceride. Although there are hardly any supply sources in the natural world of triglycerides containing arachidonic acid (synonymous with triglycerides containing triglycerides in which all or a portion of the constituent fatty acids are arachidonic acid), the inventors of the present invention made it possible to industrially utilize triglyceride containing arachidonic acid, and by using old rats more than 20 months old in a Morris water maze test, determined for the first time the effects of the active ingredient of the present invention by behavioral pharmacology analysis, clearly demonstrating that it has preventive or ameliorative action on symptoms or diseases caused by decreased brain function.

Thus, in the present invention, triglycerides can be used that contain triglycerides in which all or a portion of the constituent fatty acids are arachidonic acid (triglycerides containing arachidonic acid), the active ingredient of the present invention. Oils and fats (triglycerides) in which the proportion of arachidonic acid among all fatty acids that compose the triglyceride is 20% by weight (w/w) or more, preferably 30% by weight or more, and more preferably 40% by weight or more, are the preferable form of triglycerides that contain arachidonic acid in the case of applying to foods. Thus, in the present invention, all triglycerides can be used provided they are obtained by culturing microorganisms having the ability to produce oils and fats (triglycerides) containing arachidonic acid.

Examples of microorganisms having the ability to produce oils and fats (triglycerides) containing arachidonic acid include microorganisms belonging to the genii *Mortierella, Conidiobolus, Pythium, Phytophthora, Penicillium, Cladosporium, Mucor, Fusarium, Aspergillus, Rhodotorula, Entomophthora, Echinosporangium* and *Saprolegnia*. Examples of microorganisms belonging to the genus *Mortierella* subgenus *Mortierella* include *Mortierella elongate, Mortierella exigua, Mortierella hygrophila* and *Mortierella alpina*. Specific examples of these strains include *Mortierella elongata* IF08570, *Mortierella exigua* IF08571, *Mortierella hygrophila* IF05941 and *Mortierella alpina* IF08568, ATCC16266, ATCC32221, ATCC42430, CBS219.35, CBS224.37, CBS250.53, CBS343.66, CBS527.72, CBS529.72, CBS608.70 and CBS754.68.

All of the these strains can be acquired without restriction from the Institute for Fermentation (IFO), Osaka, Japan, the American Type Culture Collection (ATCC), USA and the Centrralbureau voor Schimmelcultures (CBS). In addition, the strain *Mortierella elongata* SAM0219 (NIBH Deposit No. FERM P 8703) (NIBH Deposit No. FERM BP 1239), which was isolated from the soil by the research group of the present invention, can also be used.

In order to culture the microbial strains used in the present invention, spores or mycelia of that microbial strain or a pre-culture liquid obtained by culturing the microbial strain in advance are inoculated into liquid or solid media. In the case of liquid media, although glucose, fructose, xylose, saccharose, maltose, soluble starch, molasses, glycerol or mannitol are typically used as a carbon source, any of these may be used and there are no restrictions on them. Examples of nitrogen sources that can be used include natural nitrogen sources such as peptones, yeast extract, wheat germ extract, beef extract, casamino acids, cornstarch stiplica, soybean protein, defatted soybean and cottonseed residue, as well as organic nitrogen sources such as urea, and inorganic nitrogen sources such as sodium nitrate, ammonium nitrate and ammonium sulfate. In addition, inorganic salts such as phosphates, magnesium sulfate, iron sulfate and copper sulfate as well as vitamins and so forth can be used as necessary as trace nutrient sources. There are no particular restrictions on these media ingredients provided they are at a concentration that does not impair microorganism growth. In practical terms, the nitrogen source should typically have a concentration of 0.1-40% by weight (w/v), and preferably 1-25% by weight (w/v). The initial amount of nitrogen source added is typically 0.1-10% by weight (w/v), and preferably 0.1-6% by weight (w/v), and the nitrogen source may be added during the course of culturing.

Moreover, oils and fats (triglycerides) having an arachidonic acid content of 45% by weight or more can also be used as the active ingredient of the present invention by controlling the concentration of the carbon source in the medium. Culturing consists of an organism growth phase extending from days 2 to 4 of culturing, and an oil or fat accumulation phase extending beyond days 2 to 4 of culturing. The initial concentration of the carbon source should be 1-8% by weight, and preferably 1-4% by weight, the carbon source should be gradually increased only during organism growth phase and early oil or fat accumulation stage, and total amount of the sequentially added carbon source should be 2-20% by weight, and preferably 5-15% by weight. Furthermore, an oil or fat (triglyceride) having an arachidonic acid content of 45% by weight or more can be obtained and used as the active ingredient of the present invention by making the gradually added amount of carbon source added during the organism growth phase and early oil or fat accumulation stage such that the concentration of carbon source in the medium becomes 0 on day 7 of culturing and beyond, preferably on day 6 of culturing and beyond, and more preferably on day 4 of culturing and beyond, by an addition corresponding to the initial concentration of the nitrogen source.

Although the culturing temperature of arachidonic acid-producing microorganisms varies according to the microorganism used, it should be 5-40° C. and preferably 20-30° C., and after growing the microorganisms by culturing at 20-30° C., culturing is continued at 5-20° C. to produce unsaturated fatty acid. The proportion of polyunsaturated fatty acids among the fatty acids formed can be increased by controlling the temperature in this manner. The pH of the medium is 4-10, and preferably 5-9, and culturing is carried out by aerated stir culturing, shake culturing or stationary culturing. Culturing is normally carried out for 2-30 days, preferably 5-20 days, and more preferably 5-15 days.

Moreover, as another means of increasing the proportion of arachidonic acid in an oil or fat (triglyceride) containing arachidonic acid besides controlling the concentration of the carbon source in the medium, oil or fat having a high content of arachidonic acid can also be obtained by selectively hydrolyzing oil or fat containing arachidonic acid. Since the lipase used for this selective hydrolysis does not have position specificity for triglycerides, and the hydrolysis activity decreases in proportion to the number of double bonds, ester bonds of fatty acids other than polyunsaturated fatty acids are hydrolyzed. The resulting triglyceride has an increased polyunsaturated fatty acid content due to the occurrence of a transesterification reaction between the resulting PUFA partial glycerides ("Enhancement of Arachidonic Acid: Selective Hydrolysis of a Single-Cell Oil from *Mortierella* with *Candida cylindracea* Lipase", J. Am. Oil Chem. Soc., 72, 1323-1327 (1998)). In this manner, an oil or fat having a high content of arachidonic acid obtained by carrying out selective hydrolysis on an oil or fat (triglyceride) containing arachidonic acid can be used as the active ingredient of the present invention. Although the proportion of arachidonic acid relative to the total amount of fatty acids of an oil or fat (triglyceride) containing arachidonic acid of the present invention is preferably high for the purpose of eliminating the effects of other fatty acids, it is not limited to a high proportion, but rather, in actuality, in the case of applying to foods, there are cases in which the absolute amount of arachidonic acid may present problems, and even oils and fats (triglycerides) having an arachidonic acid content of 10% by weight or more can substantially be used.

Moreover, triglycerides in which medium-chain fatty acids are bound at 1,3-position and arachidonic acid is bound at 2-position can also be used as a triglyceride in which all or a portion of the constituent fatty acids are arachidonic acid. In addition, oils and fats (triglycerides) can be used that contain 5 mol % or more, preferably 10 mol % or more, more preferably 20 mol % or more, and most preferably 30 mol % or more of a triglyceride in which medium-chain fatty acids are bound at 1,3-position and arachidonic acid is bound at 2-position. Medium-chain fatty acids selected from fatty acids having 6 to 12 carbon atoms can be used for the medium-chain fatty acids bound at 1,3-position of the aforementioned triglyceride. Examples of fatty acids having 6 to 12 carbon atoms include caprylic acid and capric acid, and 1,3-capryloyl-2-arachidonoyl-glycerol (to be referred to as "8A8") is particularly preferable.

These triglycerides in which medium-chain fatty acids are bound at 1,3-position and arachidonic acid is bound at 2-position are optimum oils and fats (triglycerides) in the case of being used for the elderly. Although ingested oils and fats (triglycerides) are typically hydrolyzed by pancreatic lipase when they enter the small intestine, this pancreatic lipase is specific for 1,3-position, enabling 1,3-position of the triglycerides to be severed resulting in the formation of two molecules of free fatty acid, while at the same time forming one molecule of 2-monoacylglycerol (to be referred to as "2-MG"). As this 2-MG is extremely soluble in bile acids and has a high degree of absorption, 2-position fatty acids are typically considered to be easily absorbed. In addition, when 2-MG dissolves in bile acids, it plays the role of a surfactant by acting to increase the absorption of free fatty acids. Next, the free fatty acids and 2-MG biosynthesize bile acid compound micelles together with cholesterol and phospholipids, which are then incorporated into small intestine epithelial cells where the resynthesis of triacylglycerol takes place, after which this is ultimately released into the lymph in the form of chylomicrons. However, this pancreatic lipase is highly specific for saturated fatty acids, thus giving arachidonic acid the characteristic of being resistance to severing by this enzyme. Another problem is that, since pancreatic lipase activity decreases with age, in elderly persons susceptible to symptoms and diseases caused by decreased brain function, triglycerides in which medium-chain fatty acids are bound at 1,3-position and arachidonic acid is bound at 2-position are the optimum type of oils and fats (triglycerides).

As a concrete example of a method for producing triglyceride in which medium-chain fatty acids are bound at 1,3-position and arachidonic acid is bound at 2-position, such a triglyceride can be produced by allowing lipase, which specifically acts on the ester bonds at 1,3-position of the triglyceride, to act in the presence of oil or fat (triglyceride) containing arachidonic acid and medium-chain fatty acids.

The oil or fat (triglyceride) serving as the raw material is a triglyceride that has arachidonic acid as a constituent fatty acid, and in the case the proportion of arachidonic acid relative to the total amount of fatty acids that compose the triglyceride is high, because decreases in the reaction yield can be prevented by increasing the unreacted oil or fat (triglyceride in which only the raw material triglyceride or 1,3-position fatty acids have become medium-chain fatty acids), the enzyme reaction temperature is normally higher than 20-30° C., preferably 30-50° C., and more preferably 40-50° C.

Examples of lipases that can be used which specifically act on the ester bonds at 1,3-position of triglycerides include those produced by microorganisms such as *Rhizopus* species, *Rhizomucor* species and *Aspergillus* species, as well as porcine pancreatic lipase. Commercially available products can also be used for this lipase. Examples of commercially available lipases include, but are not limited to, the lipase of *Rhizopus delemar* (Tanabe Seiyaku, Talipase), and the lipases of *Rhizomucor miehei* (Novo Nordisk, Lipozyme IM) and *Aspergillus niger* (Amano Pharmaceutical Lipase A), and any lipase can be used provided it is specific for 1,3-position.

The aforementioned lipase is preferably used in the form of lipase immobilized on a immobilizing support for the purpose of imparting heat resistance to the enzyme since the reaction temperature is 30° C. or higher, and preferably 40° C. or higher, for the purpose of enhancing reaction efficiency. An ion exchange resin support in the form of a highly porous resin having a pore diameter of about 100 Angstroms or more can be used for the immobilizing support, an example of which is the Dowex Marathon WBA (trade name, Dow Chemical).

0.5-20 parts (by weight) of an aqueous solution of 1,3-position-specific type lipase are suspended in 1 part of immobilizing support followed by the gradual addition of 2-5 parts of cold acetone (e.g., −80° C.) to the suspension while stirring to form a precipitate. An immobilized enzyme can then be prepared by drying this precipitate under reduced pressure. As an even simpler method, 0.05-0.4 parts of 1,3-position-specific type lipase are dissolved in a minimum of water and mixed with 1 part of immobilizing support while stirring followed by drying under reduced pressure to prepare an immobilized enzyme. Although about 90% of the lipase is immobilized on the support by this procedure, since it does not exhibit any transesterification activity in this state, the immobilized enzyme can be activated most efficiently by pre-treating in a solute (raw material oil or fat and medium-chain fatty acids) to which 1-10% by weight (w/v) of water has been added, and preferably in a solute to which 1-3% by weight of water has been added, followed by use in production.

Depending on the type of enzyme, the amount of water added to the reaction system is extremely crucial. The transesterification proceeds with difficulty if water is not contained in the reaction system, while hydrolysis occurs if a large amount of water is present, thereby decreasing the triglyceride recovery rate (due to the formation of diglycerides and monoglycerides by hydrolysis). In this case, however, by using an immobilized enzyme that has been activated by the aforementioned pre-treatment, the amount of water added to the reaction system is no loner important, and the transesterification reaction is able to occur efficiently even in the complete absence of water. Moreover, the pre-treatment can be omitted by selecting the type of enzyme agent.

By using an immobilized enzyme having heat resistance and increasing the enzyme reaction temperature in this manner, triglyceride in which medium-chain fatty acids are bound at 1,3-position and arachidonic acid is bound at 2-position can be efficiently produced without causing a decrease in reaction efficiency even in the case of oils and fats (triglycerides) containing arachidonic acid for which 1,3-position-specific type lipase has a low level of activity.

In the production of a food or beverage having preventive or ameliorative action on symptoms or diseases caused by decreased brain function, arachidonic acid and/or a compound having arachidonic acid as a constituent fatty acid may be used alone, or it may be blended with a food, or beverage raw material substantially free of arachidonic acid or containing only a slight amount of arachidonic acid. Here, a slight amount refers to an amount for which, even if arachidonic acid is contained in the food or beverage raw material, the food composition in which it is contained does not reach the daily ingested amount of arachidonic acid of the present invention, to be described later, when that food composition is ingested by a person.

In the case of triglycerides in which all or a portion of the constituent fatty acids are arachidonic acid in particular, there are no restrictions on the application of those oils and fats (triglycerides), and they can be used as raw materials or additives of foods, beverages, pharmaceuticals or over-the-counter drugs. These triglycerides are also not subjected to any restrictions on the purpose of their use or the amount used.

Examples of food compositions include not only ordinary foods, but also functional foods, nutritional supplement foods, newborn formulas, infant formulas, baby food, foods to be consumed during pregnancy and geriatric foods. Examples of foods that contain oils and fats include natural foods that inherently contain oils and fats such meats, fish and nuts, foods to which oils and fats are added during preparation such as soup, foods for which oils and fats are used as a heating medium such as doughnuts, oily foods such as butter, processed foods to which oils and fats are added during processing such as cookies, and foods in which oils and fats are sprayed or coated during final processing such as hard biscuits. Moreover, oils and fats can also be added to agricultural food products, fermented food products, livestock food products, marine food products or beverages that do not contain oils and fats. Moreover, these may also be in the form of functional foods, pharmaceuticals or over-the-counter drugs, examples of which include transintestinal nutrients, powders, granules, tablets, capsules, troches, medicines, suspensions, emulsions, syrups and other processed forms.

Moreover, in addition to the active ingredient of the present invention, the composition of the present invention may also contain various carriers and additives ordinarily used in foods, beverages, pharmaceuticals or over-the-counter drugs. In particular, the composition of the present invention preferably contains an antioxidant for the purpose of preventing oxidative deterioration of the active ingredient of the present invention. Examples of antioxidants include natural antioxidants such as tocopherols, flavone derivatives, phyllozulcins, kojic acid, gallic acid derivatives, catechins, butterburic acid, gossypol, pyrazine derivatives, sesamol, guaiacol, guaiac fat, p-coumaric acid, nordihydroguaiatetic acid, sterols, terpenes, nucleic acid bases, carotinoids and lignans, as well as synthetic antioxidants exemplified by such compounds as ascorbic palmitate ester, ascorbic stearate ester, butylhydroxyanisole (BHA), butylhydroxytoluene (BHT), mono-t-butylhydroxyquinone (TBHQ) and 4-hydroxymethyl-2,6-di-t-butylphenol (HMBP). Examples of tocopherols include α-tocopherol, β-tocopherol, γ-tocopherol, δ-tocopherol, ε-tocopherol, ξ-tocopherol, η-tocopherol and tocopherol esters (such as tocopherol acetate). Moreover, examples of carotinoids include β-carotene, cantaxanthine and astaxanthine.

In the composition of the present invention, in addition to the active ingredient of the present invention, examples of carriers include various immobilizing supports, extenders, diluents, thickeners, dispersants, vehicles, binder solvents (such as water, ethanol and vegetable oils), solvent assistants, buffers, solubility promoters, gelling agents, suspension agents, flour, rice flour, starch, cornstarch, polysaccharide, milk protein, collagen, rice oil and lecithin. Examples of additives include, but are not limited to, vitamins, sweeteners, organic acids, colorants, fragrances, moisture prevention agents, fibers, electrolytes, minerals, nutrients, antioxidants, preservatives, aromatics, wetting agents, natural food extracts and vegetable extracts.

The major pharmacologically active ingredient of arachidonic acid and compound having arachidonic acid as a constituent fatty acid lies in the arachidonic acid. The daily ingested amount of arachidonic acid in the diet is reported to be 0.14 g in the Kanto region and 0.19-0.20 g in the Kansai region (Lipid Nutrition Science, 4, 73-82, 1995). In consideration of the decreased ingestion of oils and fats by the elderly and the decrease in pancreatic lipase activity, elderly persons are required to ingest at least an equivalent amount, and most likely an even greater amount, of arachidonic acid. Thus, the daily ingested amount of the arachidonic acid and compound having arachidonic acid as a constituent fatty acid of the present invention for an adult (for example, body weight: 60 kg) is 0.001-20 g, preferably 0.01-10 g, more preferably 0.05-5 g and most preferably 0.1-2 g as arachidonic acid.

In the case of actually applying the active ingredient of the present invention to foods or beverages, the absolute amount of arachidonic acid blended into the food is important. However, as the absolute amount blended into the food or beverage also varies according to the ingested amount of the food or beverage in which it is blended, in the case of blending triglycerides containing a triglyceride in which all or a portion of the constituent fatty acids are arachidonic acid into a food, they should be blended so that the amount of arachidonic acid is 0.0003% by weight or more, preferably 0.003% by weight or more, and more preferably 0.03% by weight or more. Moreover, in the case of blending triglycerides containing a triglyceride in which medium-chain fatty acids are bound to 1,3-position and arachidonic acid is bound to 2-position into a food or beverage, they should be blended so that the amount of medium-chain fatty acids bound at 1,3-position is 0.001% by weight or more, preferably 0.01% by weight or more, and more preferably 0.1% by weight or more, as triglyceride in which arachidonic acid is bound at 2-position.

In the case of using the composition of the present invention as a pharmaceutical, a pharmaceutical can be produced in accordance methods ordinarily used in the field of pharmaceutical technology, such as methods described in the Japanese Pharmacopoeia or methods conforming thereto.

In the case of using the composition of the present invention as a pharmaceutical, there are no particular restrictions on the blended amount of active ingredient in the composition provided the object of the present invention is achieved, and it can be used at any suitable blending ratio.

In the case of using the composition of the present invention as a pharmaceutical, it is preferably administered in a single administration form, and oral administration is particularly preferable. Although the dosage of the composition of the present invention varies according to age, body weight, symptoms, number of administrations and so forth, for example, the daily adult dosage (body weight: approx. 60 kg) of arachidonic acid or a compound having arachidonic acid as a constituent fatty acid of the present invention is normally about 0.001-20 g, preferably about 0.01-10 g, more preferably about 0.05-5 g and most preferably about 0.1-2 g as arachidonic acid, and should be administered by dividing it among one to three administrations per day.

The major phospholipids of the phospholipid membranes in the brain are arachidonic acid and docosahexaenoic acid, and in the case of considering the balance between the two, the composition of the present invention preferably combines docosahexaenoic acid with arachidonic acid. In addition, as the proportion of eicosapentaenoic acid in the phospholipid membranes of the brain is extremely low, the composition of the present invention preferably contains hardly any eicosapentaenoic acid. In addition, a composition is more preferable that contains hardly any eicosapentaenoic acid but contains arachidonic acid and docosahexaenoic acid. In the combining of the arachidonic acid and docosahexaenoic acid, the ratio of arachidonic acid to docosahexaenoic acid (weight ratio) is within the range of 0.1-15 and preferably within the range of 0.25-10. In addition, a food or beverage is preferable in which the amount of eicosapentaenoic acid does not exceed one-fifth the amount (weight ratio) of arachidonic acid.

The following provides a more detailed explanation of the present invention through its examples. However, the present invention is not limited to the following examples.

Furthermore, health foods, functional foods, food for specified health uses, geriatric food and other food compositions of the present invention include those sold without any description or label on packaging container of said food composition and/or a marketing tool (such as a pamphlet) for promoting sales of said food composition indicating that the said food composition and/or ingredients of said food composition have preventive or ameliorative action for symptoms or diseases caused by decreased brain function, and more specifically, preventive or ameliorative action for symptoms or diseases caused by decreased brain function accompanying aging, prevention and amelioration of decreased memory or learning ability, decreased cognitive ability, emotional disorders (e.g., depression) and mental disorders (e.g., dementia, and specifically Alzheimer's dementia and cerebrovascular dementia), prevention of forgetfulness, prevention of senility, maintenance and improvement of memory, maintenance and improvement of concentration, maintenance and improvement of attentiveness, refreshing the mind, maintaining wakefulness and maintaining youth.

Example 1

Production Method of Triglycerides Containing Arachidonic Acid

*Mortierella alpina* CBS754.68 was used for the arachidonic acid-producing microorganism. Six kL of medium containing 1.8% glucose, 3.1% defatted soybean powder, 0.1% soybean oil, 0.3% $KH_2PO_4$, 0.1% $Na_2SO_4$, 0.05% $CaCl_2.2H_2O$ and 0.05% $MgCl_2.6H_2O$ were prepared in a 10 kL culturing tank and the initial pH was adjusted to 6.0. After inoculating with 30 L of pre-culture liquid, culturing was carried while aerating by stirring for 8 days under conditions of a temperature of 26° C., air flow rate of 360 $m^3$/hour and tank internal pressure of 200 kPa. Furthermore, the stirring rate was adjusted so as to maintain the dissolved oxygen concentration at 10-15 ppm. Moreover, the glucose concentration was maintained so that the glucose concentration in the medium was within the range of 1-2.5% through day 4 and 0.5-1% after that time (the above percentages refer to w/v %) using the flow addition method. Following completion of culturing, those microorganisms that contain triglycerides containing arachidonic acid were recovered by filtration and drying, and oil or fat was extracted from the resulting microorganisms with hexane followed by an edible oil purification step (degumming, deacidifying, deodorizing and decoloring) to obtain 150 kg of arachidonic acid-containing triglycerides (wherein the arachidonic acid was bound at an arbitrary site of the triglyceride). When the methyl esters were prepared from the resulting oil or fat (triglycerides) by transmethylation and analyzed by gas chromatography, the proportion of arachidonic acid in the total amount of fatty acids was 40.84% by weight. Furthermore, the proportions of palmitic acid, stearic acid, oleic acid, linoleic acid, γ-linolenic acid and dihomo-γ-linolenic acid were 11.63, 7.45, 7.73, 9.14, 2.23 and 3.27% by weight, respectively. Moreover, 99% by weight arachidonic ethyl ester was isolated and purified by the established method of high-performance liquid chromatography from a fatty acid ethyl ester mixture containing 40% by weight of arachidonic ethyl ester, prepared from the aforementioned arachidonic acid containing oil or fat (triglycerides) by transethylation.

Example 2

Production of Triglycerides Containing 5 Mol % or More of 8A8

100 g of an ion exchange resin support (Dowex Marathon WBA: Dow Chemical, trade name) were suspended in 80 ml of an aqueous solution of 12.5% *Rhizopus delemar* lipase (Talipase Powder, Tanabe Seiyaku) followed by drying under reduced pressure to obtain immobilized lipase.

Next, 80 g of the triglycerides obtained in Example 1 containing 40% by weight of arachidonic acid (TGA40S), 160 g of caprylic acid, 12 g of the aforementioned immobilized lipase and 4.8 ml of water were allowed to react for 48 hours at 30° C. while stirring (130 rpm). Following completion of the reaction, the reaction solution was removed to obtain activated immobilized lipase.

Next, 10 g of immobilized lipase (*Rhizopus delemar* lipase, support; Dowex Marathon WBA, trade name) were filled into a jacketed glass column (1.8×12.5 cm, volume: 31.8 ml), and a mixed oil or fat consisting of the TGA40S obtained in Example 1 and caprylic acid mixed at a ratio of 1:2 was allowed to flow through the column at a constant flow rate (4 ml/h) to allow the reaction to proceed continuously and obtain 400 g of reaction oil or fat. Furthermore, the column temperature was 40-41° C. Unreacted caprylic acid and free fatty acids were removed by molecular distillation to obtain an oil or fat (triglycerides) containing 8A8. When the proportion of 8A8 in the resulting 8A8-containing oil or fat (triglycerides) was investigated by gas chromatography and high-performance liquid chromatography, it was found to be 31.6 mol %. (Furthermore, the proportions of 8P8, 8O8, 8L8, 8G8 and 8D8 were 0.6, 7.9, 15.1, 5.2 and 4.8 mol %, respectively. The fatty acids P, O, L, G and D bound to 2-position of the triglyceride represent palmitic acid, oleic acid, linoleic acid, γ-linolenic acid and dihomo-γ-linolenic acid, respectively, while 8P8 refers to 1,3-capryloyl-2-palmitoyl-glycerol, 8O8 to 1,3-capryloyl-2-oleoyl-glycerol, 8L8 to 1,3-capryloyl-2-linoleoyl-glycerol, 8G8 to 1,3-capryloyl-2-γ-linolenoyl-glycerol and 8D8 to 1,3-capryloyl-2-dihomo-γ-linolenoyl-glycerol.) Furthermore, 96 mol % 8A8 was purified and isolated from the resulting 8A8-containing oil or fat (triglycerides) by the established method of high-performance liquid chromatography.

Example 3

Evaluation of Learning Ability of TGA40S by a Morris Water Maze Test

For the test groups of old rats, sixteen 18-month-old male Fischer rats were divided into two groups consisting of a control diet group (8 animals, group OC) and a TGA40S diet group (8 animals, group OA), and the control diet and SUNTGA40S diet shown in Table 1 were given to each group, respectively. The control diet shown in Table 1 was given to eight 4-month-old male Fischer rats serving as a control group of young rats (group YC). Furthermore, the TGA40S obtained in Example 1 was used for the TGA40S used in the TGA40S diet.

TABLE 1

Test Diets

| | Control Diet (g) | TGA40S Diet (g) |
|---|---|---|
| Casein | 200 | 200 |
| DL-methionine | 3 | 3 |
| Cornstarch | 150 | 150 |
| Sucrose | 500 | 500 |
| Cellulose powder | 50 | 50 |
| Corn oil | 50 | 45 |
| Mineral AIN-76 | 35 | 35 |
| Vitamin AIN-76 | 10 | 10 |
| Choline bitartrate | 2 | 2 |
| Vitamin E | 0.05 | 0.05 |
| TGA40S | 0 | 5 |

Since the daily ingested amount per rat was about 20 g, the daily ingested amount of TGA40S per rat is 0.1 g. Since 40% by weight of all of the fatty acids bound to TGA40S is arachidonic acid, this means that the daily ingested amount of arachidonic acid per rat is 40 mg (the weight of the glycerol skeleton was ignored to simplify calculations). This 40 mg is equivalent to 133 mg/60 kg/day when converted to the ingested amount for humans.

Figure 2:
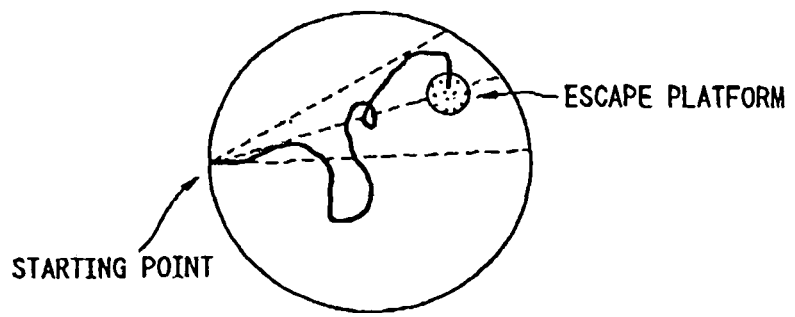
FIG. 2 provides an explanation of learning acquisition (Hit %).
Figure 3:
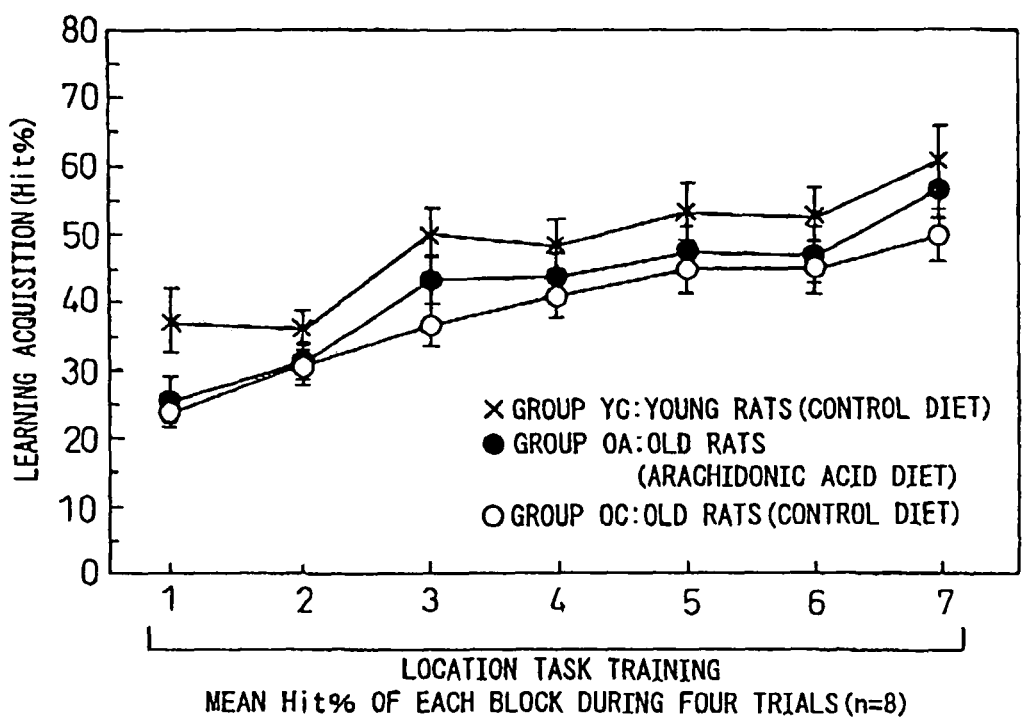
FIG. 3 is a graph showing learning acquisition relative to the number of trials made by rats.

A Morris water maze learning test was conducted around the third month of the experiment (age of old rats: 21 months, age of young rats: 7 months). The Morris water maze test is a learning test based on spatial recognition in which water stained black with ink is filled (height of water level: 20 cm) into a water tank (diameter: 120 cm, height: 35 cm), a rat is placed on an escape platform of a size (diameter: 11.5 cm, height: 19 cm) that is just large enough for the rat to stand on (the escape platform is located beneath the surface of the water and cannot be seen by rats swimming in the water tank), the rat on which the learning test is to be performed is placed in the water tank at a predetermined location in the tank (starting point), and then forced to swim to the escape platform. This test is recognized to have a correlation with the hippocampus that governs memory, and is widely used in the US and Europe. As the test is repeated, the rats learn the location of the escape platform. The rats were allowed to learn using the method described below. Namely, after releasing a rat from the starting point of the Morris water maze test apparatus, if the rat was unable to reach the escape platform within 60 seconds, the rat was placed on the escape platform, thereby enabling it to learn the location of the unseen escape platform. This learning process was continued for 2 weeks no more than twice a day. The percentage of the amount of time required to swim from the starting point to the escape platform within an angular deviation range of ±15° to the total swimming time (Hit %, see FIG. 2) was used as an indicator of learning. Although the learning acquisition rate of old rats clearly decreases as compared with young rats, as a result of feeding TAG40S, namely arachidonic acid, learning acquisition rate improved to near the level of young rats (FIG. 3). In FIG. 3, each graduation on the scale of the horizontal axis represents four trials, or two days worth of testing.

Figure 4:
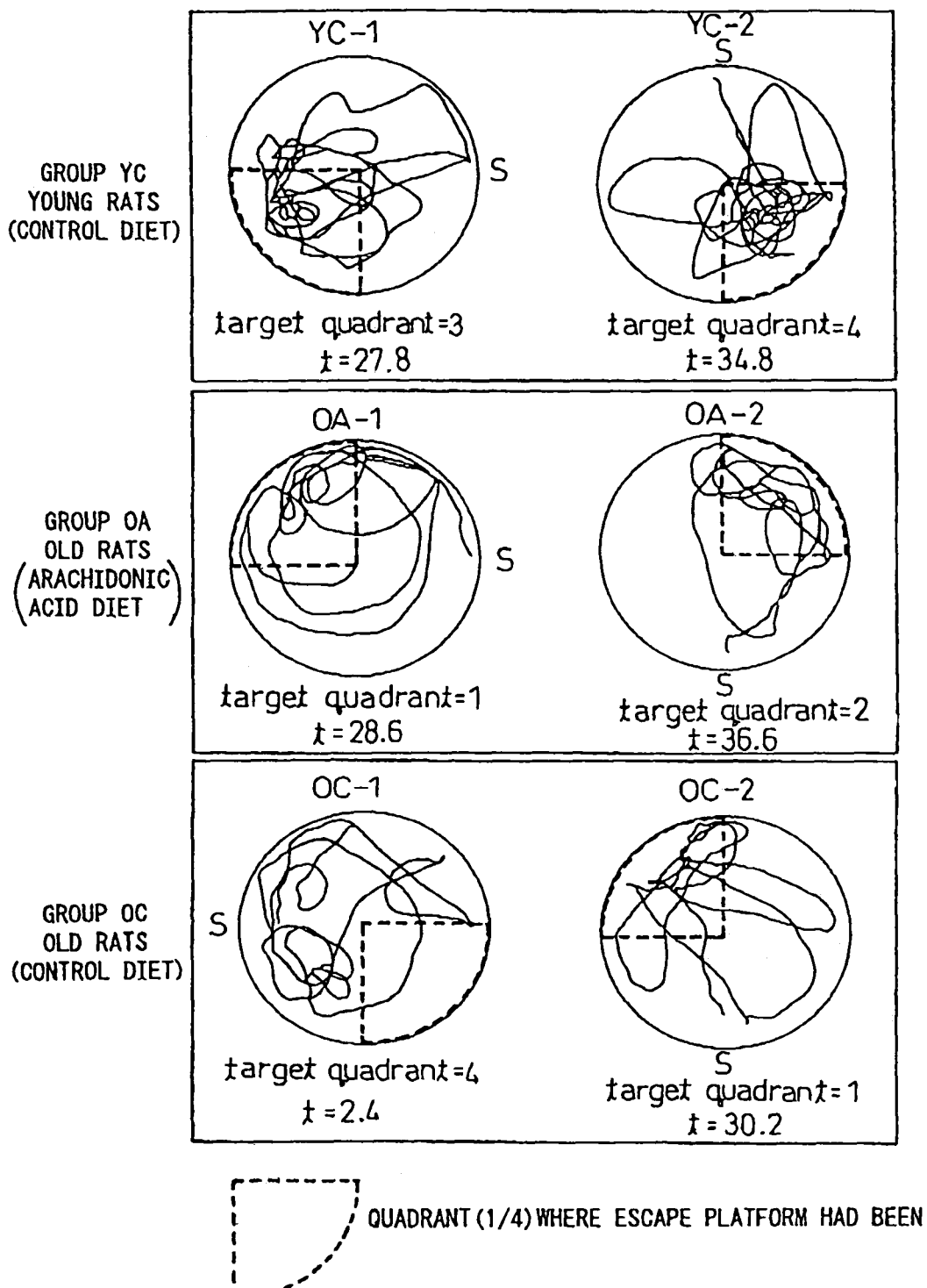
FIG. 4 is a drawing showing the paths swam by rats for 60 seconds in a probe test for determining the degree of learning acquisition.
Figure 5:
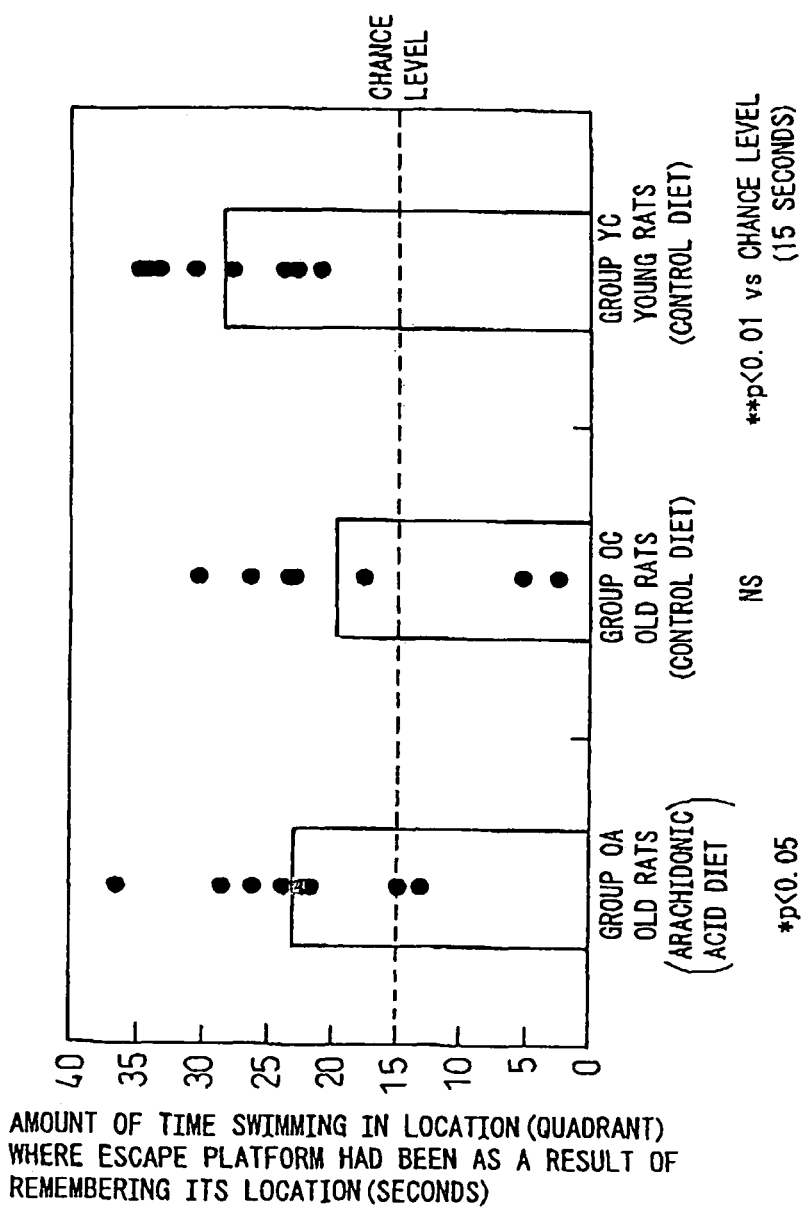
FIG. 5 is a graph showing the results of a probe test for determining the degree of learning acquisition.

Next, in order to determine the degree of learning acquisition, a probe test was conducted on the day after two weeks of the aforementioned learning, namely on day 15. If the escape platform is taken away after the rats have acquired learning, the rats swim around at the location where the escape platform used to be. The time during which the rats swim around at the former location of the escape platform based on the memory of where it used to be (evaluated by dividing the water tank into four quadrants and evaluated as the amount of time (seconds) spent in the quadrant where the escape platform used to be) can be used to evaluate the degree of learning acquisition. The paths swam by the No. 1 and No. 2 rats of the YC group, OA group and OC group are shown (FIG. 4). Furthermore, as the rats were allowed to learn by changing the starting points for individual rats, the starting point (S) and quadrant where the escape platform used to be in FIG. 4 differ according to individual rats. In addition, in FIG. 5, target quadrant indicates the quadrant (¼) where the escape platform used to be. Rat OC-1 of the OC group was clearly wandered throughout the water tank, and was only in the quadrant where the escape platform used to be for 2.4 seconds. The results of the probe test are summarized in Table 2.

TABLE 2

Results of Probe Test

| Test Group | Time swimming at location where escape platform used to be as a result of remembering location of escape platform (sec.) n = 8 | Mean ± standard deviation (SD) | Sample standard deviation (S) | t value | p value (from t(f:p) table) degree of freedom f = n − 1 = 7 |
|---|---|---|---|---|---|
| Group OA | 28.6, 36.6, 14.8, 22.2, 22.2, 26.2, 13.0, 21.8 | 23.20 ± 7.54$^{ab*}$ | 7.06 | 3.07 | p < 0.05 |
| Group OC | 2.4, 30.2, 23.4, 17.4, 5.0, 23.0, 30.4, 26.4 | 19.78 ± 10.79$^{b}$ | 10.09 | 1.25 | — |

TABLE 2-continued

Results of Probe Test

| Test Group | Time swimming at location where escape platform used to be as a result of remembering location of escape platform (sec.) n = 8 | Mean ± standard deviation (SD) | Sample standard deviation (S) | t value | p value (from t(f:p) table) degree of freedom f = n − 1 = 7 |
|---|---|---|---|---|---|
| Group YC | 27.8, 34.8, 30.6, 33.4, 20.8, 23.4, 34.0, 22.6 | 28.43 ± 5.59$^a$ | 5.23 | 6.79 | p < 0.001 |

*$^a$ and $^b$ indicate a significant difference between different letters (p < 0.05)

a and b indicate a significant difference between different letters (p<0.05)

In Table 2, $$t = \frac{\overline{X} - \mu}{\frac{S}{\sqrt{n-1}}}$$

where,
$\overline{X}$
represents the mean, μ the population mean (15 seconds), S the sample standard deviation, SD the mean± standard deviation and n the number of data elements (number of data elements of each group), while S represents $$S = \sqrt{\frac{\sum_{i=1}^{n}(X_i - \overline{X})}{n}}$$

and SD represents $$SD = \sqrt{\frac{\sum_{i=1}^{n}(X_i - \overline{X})}{n-1}}$$

When Table 2 is expressed in the form of a graph (FIG. 5), the amount of time spent in the quadrant where the escape platform used to be by the old rats of group OA given TGA40S (time spent swimming around the location where the escape platform used to be as a result of remembering the location of the escape platform) can be seen to be significantly longer. As the chance level of 15 seconds measures the time spent by allowing the rats to swim for 60 seconds, this also indicates the possibility of the rats spending time in that quadrant by coincidence. The bar graph indicates the mean time spent by rats in the quadrant where the escape platform used to be.

Figure 6:
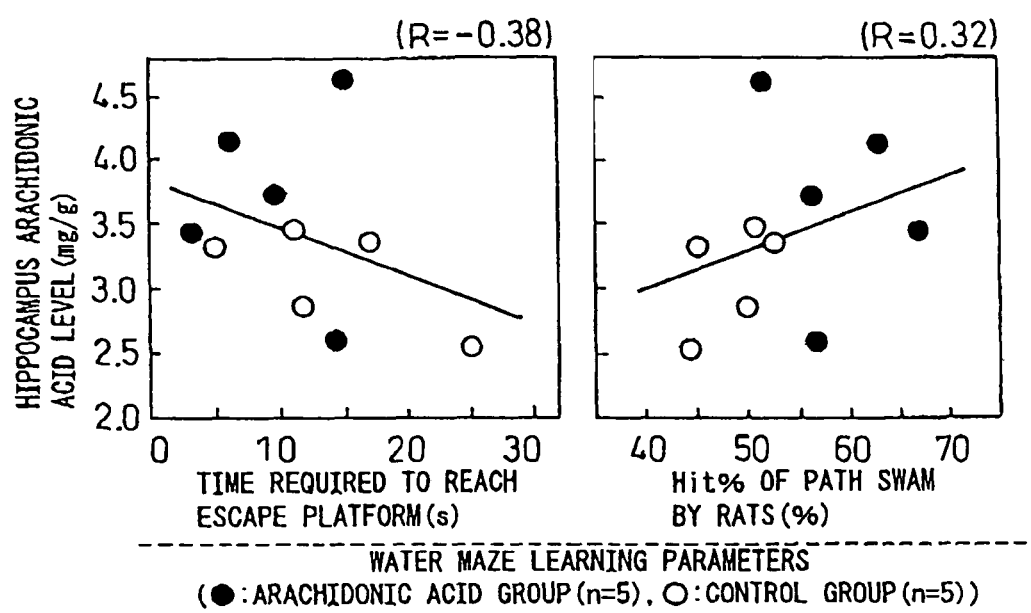
FIG. 6 is a graph showing the results of determining the correlation between learning parameters and arachidonic levels in the hippocampus.

Next, the hippocampus was excised from those rats used in the Morris water maze test and all of the lipids were extracted using the Folch method. After then fractioning the lipids by thin layer chromatography, scraping off the phospholipid fraction and removing the water by boiling with ethanol, the lipids were analyzed by gas chromatography after converting to fatty acid methyl esters with 10% hydrochloric acid-methanol. As a result of determining the correlation between the water maze learning parameters ("time to reach escape platform (the shorter the better)", "proportion of time swimming toward escape platform (Hit %, the larger the better)") and the amount of arachidonic acid in the hippocampus with a primary approximation curve based on the least squares method (FIG. 6), a negative correlation was observed between time to reach escape platform and amount of arachidonic acid in hippocampus (correlation coefficient R=−0.38), while a positive correlation was observed between time to reach escape platform and Hit % of the path swam by the rats (correlation coefficient R=0.32). In FIG. 6, the vertical axis indicates the amount of arachidonic acid in mg per gram of hippocampus tissue. In this manner, it was shown for the first time that the administration of TGA40S improves learning ability or cognitive ability, and it was also demonstrated for the first time that the effect is due to arachidonic acid.

Example 4

Evaluation of Learning Ability of 8A8 by a Morris Water Maze Test

For the test groups of old rats, twenty 18-month-old male Fischer rats were divided into three groups consisting of a control diet group (6 animals, group OC), a TGA40S diet group (6 animals, group OA) and an 8A8 diet group (8 animals, group 8A8), and the control diet, SUNTGA40S diet and 8A8 diet shown in Table 3 were given to each group, respectively. The control diet shown in Table 3 was given to eight 4-month-old male Fischer rats serving as a control group of young rats (group YC). Furthermore, the 96 mol % 8A8 obtained in Example 2 was used for the 8A8 used in the 8A8 diet.

TABLE 3

Test Diets

|  | Control Diet (g) | TGA40S Diet (g) | 8A8 Diet (g) |
|---|---|---|---|
| Casein | 200 | 200 | 200 |
| DL-methionine | 3 | 3 | 3 |

TABLE 3-continued

| | Test Diets | | |
|---|---|---|---|
| | Control Diet (g) | TGA40S Diet (g) | 8A8 Diet (g) |
| Cornstarch | 150 | 150 | 150 |
| Sucrose | 500 | 500 | 500 |
| Cellulose powder | 50 | 50 | 50 |
| Corn oil | 50 | 45 | 45.8 |
| Mineral AIN-76 | 35 | 35 | 35 |
| Vitamin AIN-76 | 10 | 10 | 10 |
| Choline bitartrate | 2 | 2 | 2 |
| Vitamin E | 0.05 | 0.05 | 0.05 |
| TGA40S | 0 | 5 | 0 |
| 8A8 | 0 | 0 | 4.2 |

Since the daily ingested amount per rat was about 20 g, the daily ingested amount of TGA40S per rat is 0.1 g. Since 40% by weight of all of the fatty acids bound to TGA40S is arachidonic acid, this means that the daily ingested amount of arachidonic acid per rat is 40 mg (the weight of the glycerol skeleton was ignored to simplify calculations). Since the molecular weight of TGA40S is 928.5 (calculated from mean fatty acid molecular weight) and the molecular weight of 8A8 is 628.7, the test diet was designed so that the daily ingested amount of arachidonic acid pear animal was 40 mg in the 8A8 diet group as well.

A Morris water maze learning test was conducted around the third month of the experiment (age of old rats: 21 months, age of young rats: 7 months).

As a result of conducting a probe test, the times spent swimming around the location where the escape platform used to be as a result of remembering the location of the escape platform (evaluated as the amount of time (seconds) spent in the quadrant (¼) where the escape platform used to be after dividing the water tank into four quadrants) were $28.59\pm5.44^a$, $13.27\pm7.89^b$, $22.02\pm5.35^c$ and $27.18\pm5.10^{ac}$ (values: mean±standard deviation, a, b and c indicate a significant difference between different letters (P<0.05)) for group YC, group OC, group OA and group 8A8, respectively. Thus, as a result of administering triglyceride having arachidonic acid as a constituent fatty acid, the degree of learning acquisition that was decreased due to aging was significantly improved towards the level of young rats. With respect to a comparison between TGA40S and 8A8, 8A8 tended to result in a higher degree of learning acquisition. Since the ingested amounts of arachidonic acid by the rats was the same for both group OA and group 8A8, 8A8 was indicated as being more easily absorbed than TGA40S, and was demonstrated to be effective for pancreatic lipase for which activity has decreased due to aging.

Example 5

Evaluation of Learning Acquisition of Triglyceride Containing at Least 5% 8A8 by a Morris Water Maze Test For the test groups of old rats, twenty 18-month-old male Fischer rats were divided into three groups consisting of a control diet group (6 animals, group OC), a 8A8 diet group (6 animals, group 8A8) and an 8A8-containing oil or fat diet group (8 animals, group 8A8 (32 mol %)), and the control diet, 8A8 diet and 8A8-containing oil or fat diet shown in Table 4 were given to each group, respectively. The control diet shown in Table 4 was given to eight 4-month-old male Fischer rats serving as a control group of young rats (group YC). Furthermore, the oil or fat (triglycerides) containing 31.6 mol % 8A8 obtained in Example 2 was used for the 8A8-containing oil or fat (triglycerides) used for the 8A8-containing oil or fat diet.

TABLE 4

| | Test Diets | | |
|---|---|---|---|
| | Control Diet (g) | 8A8 diet (g) | 8A8-containing oil or fat diet (g) |
| Casein | 200 | 200 | 200 |
| DL-methionine | 3 | 3 | 3 |
| Cornstarch | 150 | 150 | 150 |
| Sucrose | 500 | 500 | 500 |
| Cellulose powder | 50 | 50 | 50 |
| Corn oil | 50 | 45.8 | 45.8 |
| Mineral AIN-76 | 35 | 35 | 35 |
| Vitamin AIN-76 | 10 | 10 | 10 |
| Choline bitartrate | 2 | 2 | 2 |
| Vitamin E | 0.05 | 0.05 | 0.05 |
| 8A8 | 0 | 4.2 | 0 |
| 8A8-containing oil | 0 | 0 | 4.2 |

The 8A8 diet was the same as that in Example 4, and the daily ingested amount of arachidonic acid per rat was 40 g. In the case of the 8A8-containing oil or fat (triglycerides) diet, the daily ingested amount of arachidonic acid per rat was 13.2 mg.

A Morris water maze learning test was conducted around the third month of the experiment (age of old rats: 21 months, age of young rats: 7 months).

As a result of conducting a probe test, the times spent swimming around the location where the escape platform used to be as a result of remembering the location of the escape platform (evaluated as the amount of time (seconds) spent in the quadrant (¼) where the escape platform used to be after dividing the water tank into four quadrants) were $27.91\pm5.93^a$, $13.75\pm7.74^b$, $27.00\pm4.65^c$ and $21.18\pm4.89^c$ (values: mean±standard deviation, a, b and c indicate a significant differences between different letters (P<0.05)) for group YC, group OC, group 8A8 and group 8A8 (32 mol %), respectively. Thus, as a result of administering oil or fat (triglycerides) containing at least 5% 8A8, the degree of learning acquisition that was decreased due to aging was significantly improved towards the level of young rats. However, the degree of acquisition was clearly lower than the 8A8 diet group, demonstrating that the degree of learning acquisition is dependent on the concentration of 8A8, and more specifically, on the concentration of arachidonic acid.

Example 6

Preparation of Capsules Containing Oil or Fat (Triglycerides) Containing Arachidonic Acid 100 parts by weight of gelatin and 35 parts by weight of food additive glycerin were dissolved at 50-60° C. by addition of water to prepare a gelatin coating having viscosity of 2000 cp. Next, 0.05% by weight of vitamin E oil were mixed into the arachidonic acid-containing oil or fat (triglycerides) obtained in Example 1 to prepare Capsule Contents 1. 0.05% by weight of vitamin E oil were mixed into the oil or fat (triglycerides) containing 32 mol % of 8A8 obtained in Example 2 to prepare Capsule Contents 2. 50% by weight of the arachidonic acid-containing oil or fat (triglycerides) obtained in Example 1 and 50% by weight of fish oil (tuna oil in which the proportions of eicosapentaenoic acid and docosahexaenoic acid to the total amount of fatty acids were 5.1% by weight and 26.5% by weight, respectively) were mixed followed by mixing in 0.05% by weight of vitamin E oil to prepare Capsule Contents 3. 80% by weight of the arachidonic acid-containing oil or fat (triglycerides) obtained in Example 1 and 20% by weight of fish oil (tuna oil in which the proportions of eicosapentaenoic acids and docosahexaenoic acid to the total amount of fatty acid were 5.1% by weight and 26.5% by weight, respectively) were mixed followed by mixing in 0.05% by weight of vitamin E oil to prepare Capsule Contents 4. Capsules were formed and dried in accordance with ordinary methods using these Capsule Contents 1 through 4 to produce soft capsules containing 180 mg of contents per capsule.

Example 7

Application to a Fat Infusion Agent

After adding 400 g of the oil or fat (triglycerides) containing 32 mol % 8A8 obtained in Example 2, 48 g of purified egg yolk lecithin, 20 g of oleic acid, 100 g of glycerin and 40 ml of 0.1 N sodium hydroxide and dispersing with a homogenizer, distilled water for injection was added to bring to a volume of 4 liters. This was then emulsified with a high-pressure spraying emulsifier to prepare a lipid latex. After adding 200 ml aliquots of this lipid latex to plastic bags, the plastic bags were sterilized by high-pressure steam for 20 minutes at 121° C. to obtain fat infusion agents.

Example 8

Application to a Juice 2 g of β-cyclodextrin were added to 20 ml a 20% aqueous ethanol solution followed by the addition of 100 mg of the arachidonic acid-containing triglycerides (containing 0.05% by weight vitamin E) obtained in Example 1 while stirring with a stirrer and incubating for 2 hours at 50° C. After being allowed to cool to room temperature (about 1 hour), the mixture was additionally incubated for 10 hours at 4° C. while continuing to stir. After recovering the resulting precipitate by centrifugal separation and washing with n-hexane, the product was freeze-dried to obtain 1.8 g of a cyclodextrin inclusion compound containing arachidonic acid-containing triglycerides. 1 g of this powder was then uniformly mixed with 10 L of juice to prepare a juice containing arachidonic acid-containing triglycerides.

What is claimed is:

1. A method of treating or ameliorating decreased learning ability, decreased cognitive ability, or decreased memory, each of which is caused by decreased brain function accompanying aging in a subject, the method comprising administering to said subject a composition comprising arachidonic acid and/or a compound having arachidonic acid as a constituent fatty acid in a therapeutically effective amount to treat or ameliorate said decreased learning ability, decreased cognitive ability, or decreased memory accompanying aging,
  wherein the subject is human, and wherein the therapeutically effective amount for a human adult represents a daily arachidonic acid intake of 0.05-5 g.

2. The method of treating or ameliorating of claim 1, wherein the compound having arachidonic acid as a constituent fatty acid is an alcohol ester of arachidonic acid or a triglyceride, phospholipid or glycolipid in which all or a portion of the constituent fatty acids are arachidonic acid.

3. The method of treating or ameliorating of claim 2, wherein the triglyceride in which all or a portion of the constituent fatty acids are arachidonic acid is a triglyceride in which medium-chain fatty acids are bound to 1,3-position and arachidonic acid is bound to 2-position.

4. The method of treating or ameliorating of claim 3, wherein the medium-chain fatty acids are selected from fatty acids having 6 to 12 carbon atoms.

5. The method of treating or ameliorating of claim 4, wherein the medium-chain fatty acids are selected from fatty acids having 8 carbon atoms.

6. The method of treating or ameliorating of claim 1, wherein said compound comprises triglycerides in which all or a portion of the constituent fatty acids are arachidonic acid.

7. The method of treating or ameliorating of claim 6, wherein the proportion of arachidonic acid in the triglycerides in which all or a portion of the constituent fatty acids are arachidonic acid is 10% by weight or more relative to all of the fatty acids that compose the triglycerides.

8. The method of treating or ameliorating of claim 6, wherein the triglycerides in which all or a portion of the constituent fatty acids are arachidonic acid are extracted from a microorganism belonging to the genus *Mortierella*.

9. The method of treating or ameliorating of claim 6, wherein the triglycerides in which all or a portion of the constituent fatty acids are arachidonic acid are triglycerides that are substantially free of eicosapentaenoic acid.

10. The method of treating or ameliorating of claim 1, wherein said compound comprises triglycerides containing 5 mol % or more of triglycerides in which medium-chain fatty acids are bound to 1,3-position and arachidonic acid is bound to 2-position.

11. The method of treating or ameliorating of claim 10, wherein the medium-chain fatty acids are selected from fatty acids having 6 to 12 carbon atoms.

12. The method of treating or ameliorating of claim 10, wherein the medium-chain fatty acids are selected from fatty acids having 8 carbon atoms.

13. The method of treating or ameliorating of claim 1, wherein decreased memory or decreased learning ability is treated or ameliorated.

14. The method of treating or ameliorating of claim 1, wherein decreased cognitive ability is treated or ameliorated.

15. The method of treating or ameliorating of claim 1, wherein the composition is a food composition or a pharmaceutical composition.

16. The method of treating or ameliorating of claim 1, wherein said composition additionally comprises docosahexaenoic acid and/or a compound having docosahexaenoic acid as a constituent fatty acid.

17. The method of treating or ameliorating of claim 16, wherein the compound having docosahexaenoic acid as a constituent fatty acid is an alcohol ester of docosahexaenoic acid or a triglyceride, phospholipid or glycolipid in which all or a portion or the constituent fatty acids are docosahexaenoic acid.

18. The method of treating or ameliorating of claim 16, wherein the ratio (weight) of arachidonic acid to docosahexaenoic acid in the combination of arachidonic acid and docosahexaenoic acid is within the range of 0.1 to 15.

19. The method of treating or ameliorating of claim 1, wherein either the composition comprises no eicosapentaenoic acid, or the composition comprises eicosapentaenoic acid at the amount not exceeding one-fifth of the amount of arachidonic acid in the composition.

20. The method of treating or ameliorating of claim 1, wherein the therapeutically effective amount for a human adult represents a daily arachidonic acid intake of 0.1-2 g.

* * * * *